(12) United States Patent
Raijman et al.

(10) Patent No.: US 11,471,654 B2
(45) Date of Patent: Oct. 18, 2022

(54) DILATION DEVICE AND METHOD OF USE

(71) Applicant: ProjectD, LLC, Houston, TX (US)

(72) Inventors: Isaac Raijman, Houston, TX (US); Christen Springs, Houston, TX (US)

(73) Assignee: ProjectD, LLC, Houston, TX (US)

( * ) Notice: Subject to any disclaimer, the term of this patent is extended or adjusted under 35 U.S.C. 154(b) by 103 days.

(21) Appl. No.: 16/430,246

(22) Filed: Jun. 3, 2019

(65) Prior Publication Data

US 2019/0366059 A1 Dec. 5, 2019

Related U.S. Application Data

(60) Provisional application No. 62/679,194, filed on Jun. 1, 2018.

(51) Int. Cl.
*A61M 25/10* (2013.01)
*A61B 17/12* (2006.01)
(Continued)

(52) U.S. Cl.
CPC ... *A61M 25/1002* (2013.01); *A61B 17/12136* (2013.01); *A61M 25/1025* (2013.01);
(Continued)

(58) Field of Classification Search
CPC .............. A61M 29/00; A61M 29/02; A61M 2029/025; A61M 25/0026; A61M 25/0028; A61M 25/003; A61M 2025/0031; A61M 25/0067; A61M 25/0054; A61M 25/04; A61M 25/10; A61M 25/0071; A61M 2025/0079; A61M 2025/018; A61M 25/09; A61M 2025/09008; A61M 25/09041;
(Continued)

(56) References Cited

U.S. PATENT DOCUMENTS 3,848,602 A * 11/1974 Gutnick ............... A61B 17/42
606/193
5,352,199 A * 10/1994 Tower .................. A61M 29/02
604/103.07
(Continued)

FOREIGN PATENT DOCUMENTS

CN 2395737 Y 9/2000
CN 101239215 A 8/2008
(Continued)

OTHER PUBLICATIONS

European Patent Application No. 19811046.2; Extended Search Report; dated Mar. 11, 2022; 8 pages.

*Primary Examiner* — Julian W Woo
(74) *Attorney, Agent, or Firm* — BakerHostetler

(57) ABSTRACT

The disclosure provides for a device and method for dilation. The dilation device may include a catheter body having a proximal portion and a distal portion, a dilation expandable body in fluid communication with a first opening on the distal portion of the catheter body, and an occlusion anchor expandable body in fluid communication with a second opening on the distal portion of the catheter body. The method for dilating a stricture site may include inserting the dilation device into a stricture site of a patient, expanding the occlusion anchor expandable body at the stricture site, and expanding the dilation expandable body at the stricture site.

21 Claims, 23 Drawing Sheets

(51) Int. Cl.
  *A61M 29/02*    (2006.01)
  *A61B 1/018*    (2006.01)

(52) U.S. Cl.
  CPC ............. *A61M 29/02* (2013.01); *A61B 1/018* (2013.01); *A61B 2017/1205* (2013.01); *A61M 25/1018* (2013.01)

(58) Field of Classification Search
  CPC ......... A61M 2025/09125; A61M 2025/09166; A61M 25/0125; A61M 25/1002; A61M 25/1006; A61M 25/1011; A61M 2025/1013; A61M 2025/1015; A61M 25/1018; A61M 25/10181; A61M 25/10183; A61M 25/10184; A61M 25/104; A61M 2025/1056; A61M 2025/1059; A61M 2025/1068; A61M 2025/1079; A61M 2039/0235; A61M 2039/0238; A61M 2039/0273; A61M 2039/0297; A61M 2039/062; A61M 2039/0626; A61M 25/1025; A61F 2/95; A61F 2/958; A61B 17/12136; A61B 17/12022; A61B 17/12; A61B 1/018; A61B 2017/1205; A61B 2017/22069; A61B 17/1204; A61B 17/12099; A61B 2017/00818
  See application file for complete search history.

(56) References Cited

U.S. PATENT DOCUMENTS

| | | | |
|---|---|---|---|
| 5,836,951 A | | 11/1998 | Rosenbluth et al. |
| 6,488,653 B1 | | 12/2002 | Lombardo |
| 6,692,484 B1 | | 2/2004 | Karpiel et al. |
| 6,733,474 B2 | * | 5/2004 | Kusleika ............ A61M 25/1011 604/101.02 |
| 6,743,208 B1 | | 6/2004 | Coyle |
| 6,953,431 B2 | * | 10/2005 | Barthel .............. A61B 1/00082 600/104 |
| 7,066,905 B2 | | 6/2006 | Squire et al. |
| 7,108,826 B2 | | 9/2006 | Wang et al. |
| 7,591,830 B2 | * | 9/2009 | Rutter ................. A61M 25/104 128/207.15 |
| 7,655,021 B2 | | 2/2010 | Brasington et al. |
| 8,382,787 B2 | | 2/2013 | Burton et al. |
| 8,585,959 B2 | | 11/2013 | Burton |
| 8,764,705 B2 | | 7/2014 | Hennessey |
| 8,899,225 B2 | | 12/2014 | Bosel |
| 9,011,374 B2 | | 4/2015 | Lentz et al. |
| 9,084,875 B2 | | 7/2015 | Burton |
| 9,095,688 B2 | | 8/2015 | Burton |
| 9,192,747 B2 | | 11/2015 | Hardert |
| 9,295,822 B2 | | 3/2016 | Aggerholm |
| 9,302,079 B2 | | 4/2016 | Burton et al. |
| 9,339,442 B2 | | 5/2016 | Tai et al. |
| 9,604,036 B2 | | 3/2017 | Burton et al. |
| 9,616,204 B2 | | 4/2017 | Baxter et al. |
| 9,924,948 B2 | * | 3/2018 | Burnett ............ A61B 17/12022 |
| 9,937,331 B2 | | 4/2018 | Burton et al. |
| 9,956,383 B2 | | 5/2018 | Schaeffer et al. |
| 9,956,384 B2 | * | 5/2018 | Charlebois ........ A61M 25/1025 |
| 10,016,212 B2 | | 7/2018 | Burton et al. |
| 2004/0059179 A1 | | 3/2004 | Maguire et al. |
| 2004/0089307 A1 | | 5/2004 | Brain |
| 2005/0059931 A1 | | 3/2005 | Garrison et al. |
| 2005/0149100 A1 | * | 7/2005 | Foltz ............... A61M 25/10182 606/192 |
| 2007/0203445 A1 | * | 8/2007 | Kaye .................... A61M 29/00 604/6.16 |
| 2009/0281379 A1 | * | 11/2009 | Binmoeller ............ A61B 17/11 600/106 |
| 2014/0046357 A1 | | 2/2014 | Neoh |
| 2015/0246211 A1 | | 9/2015 | Bunch et al. |
| 2016/0106940 A1 | | 4/2016 | Bosel |
| 2017/0043142 A1 | | 2/2017 | Bareau |

FOREIGN PATENT DOCUMENTS

| | | |
|---|---|---|
| CN | 105343992 A | 2/2016 |
| CN | 107198811 A | 9/2017 |
| WO | WO 2017/044991 A1 | 3/2017 |
| WO | WO 2018/071065 A1 | 4/2018 |
| WO | WO 2018/089773 A1 | 5/2018 |

\* cited by examiner

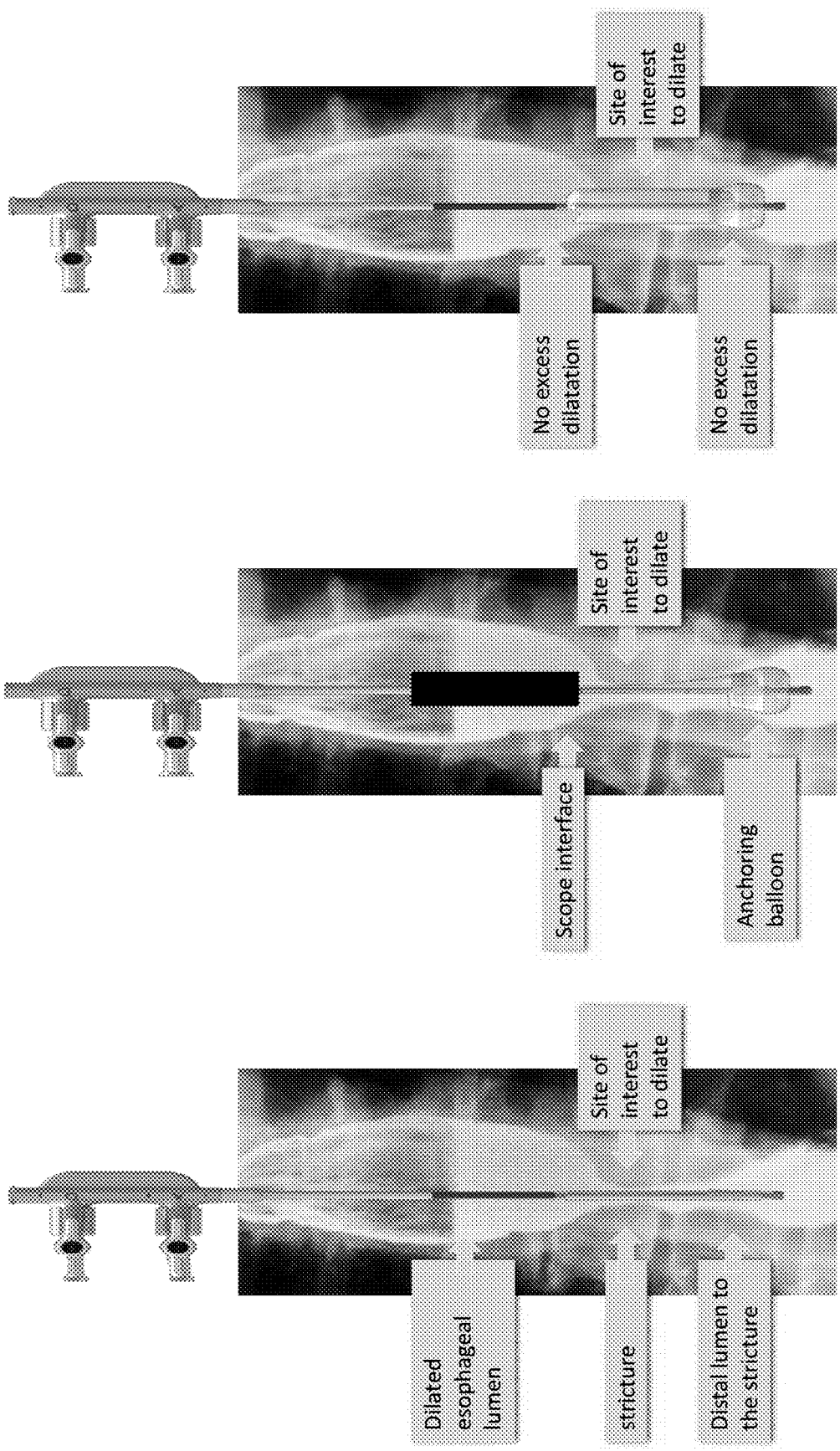

DILATION DEVICE AND METHOD OF USE

CROSS-REFERENCE TO RELATED PATENT APPLICATION

This patent application claims the benefit under 35 U.S.C. § 119(e) of U.S. Patent Application Ser. No. 62/679,194, entitled "DILATION DEVICE AND METHOD OF USE," filed on Jun. 1, 2018, which is incorporated herein by reference in its entirety.

FIELD

The present disclosure is directed to a device for balloon dilation of a GI stricture site and methods of use.

BACKGROUND

A stricture or narrowing of the gastrointestinal (GI) tract can occur at various points, including the esophagus, colon, biliary tract, due to a variety of conditions affecting the GI tract. To reduce or treat the stricture, GI endoluminal dilation may be necessary. Three general types of dilators are currently used in various areas of GI endoluminal dilation which include mercury or tungsten-filled bougies, wire-guided polyvinyl dilators, or "through-the-scope" balloon dilators. Balloon dilators are available in single or multiple diameters. Because of the limited diameter availability, sometimes multiple balloon catheters have to be inserted sequentially to achieve the desired dilation.

For esophageal or colon dilation, the current balloon dilators are either not available or unsafe to be dilated to a larger diameter (i.e. greater than 15 mm) or do not provide incremental dilation with a single balloon. In addition, the current dilators are often longer than the stricture site to accommodate for slippage of the dilation balloon that may occur during the dilation process. Thus, they tend to over dilate areas around the stricture site.

Accordingly, there remains a need in developing a device for GI endoluminal dilation to reduce or eliminate the slippage or migration of the dilation balloon and provide a wider range of dilation diameters to reduce the number of procedures needed. These and other needs are provided in this disclosure.

BRIEF SUMMARY

The disclosure provides for a dilation device including a catheter body having a proximal portion and a distal portion, a dilation expandable body in fluid communication with a first opening on the catheter body, and an occlusion anchor expandable body in fluid communication with a second opening on the catheter body.

The catheter body may include at least two lumina, each lumina may be in fluid communication with an opening on the catheter body. In a variation, the catheter may include an opening on the distal portion of the catheter body for the delivery of a dye. The catheter may further include an opening on the distal portion of the catheter body for the use of a guide wire or delivery of a dye. The dilation expandable body may be configured to receive a fluid or gas from the catheter body. The occlusion anchor expandable body may be configured to receive a fluid or gas from the catheter body. In some variations, the fluid or gas used to fill the dilation expandable body or the occlusion anchor expandable body may be pressurized.

The dilation expandable body includes a proximal end and a distal end. In some variations the dilation expandable body may further include circumferential or longitudinal ribs on the outer surface. In another variation, the dilation expandable body may include a bulb on the proximal end, the distal end, or both. The dilation device may further include at least two ports connected to the proximal portion of the catheter body, each port may be in fluid communication with at least one of the lumina of the catheter body. The at least two ports may be located on a manifold connected to the proximal portion of the catheter body. The dilation expandable body expands to a diameter of about 0.05 mm to about 25 mm. The occlusion anchor expandable body expands to a diameter of about 0.5 mm to about 25 mm. The dilation expandable body is about 2-5 cm in length. The dilation expandable body and the occlusion anchor expandable body may be made of polyether block amide (Pebax®), polyurethane, or a blend of polyurethane with another polymer. The dilation expandable body and the occlusion anchor expandable body may include at least one radiopaque marker.

The dilation expandable body and the occlusion anchor expandable body are each attached to the catheter body. The occlusion anchor expandable body may extend over at least a portion of the dilation expandable body. The occlusion anchor expandable body may surround the dilation expandable body such that the dilation expandable body is inside the occlusion anchor expandable body. The occlusion anchor expandable body may include at least one bulb at the proximal and/or distal end of the occlusion anchor expandable body. For example, the occlusion anchor expandable body includes a proximal bulb and a distal bulb. The length of each bulb may be 1 cm or less. The dilation expandable body may have a net treatment length of 1 cm to 4 cm. The occlusion anchor expandable body is operable to reduce migration of the dilation expandable body at the proximal or distal ends of the stricture site when expanded in the stricture site as compared to a standard, unanchored dilation balloon. The dilation device is operable to eliminate migration of the dilation expandable body when expanded as compared to a standard, unanchored dilation balloon. The dilation device is operable to dilate the stricture site while reducing excess dilation outside the stricture site when the dilation expandable body is expanded as compared to a standard, unanchored dilation balloon. The dilation expandable body, when expanded, may extend no more than 1 cm beyond the stricture site in either the proximal or distal direction. The dilation device of any one of the preceding claims, wherein the dilation expandable body has an inflation range of at least 3 mm to at least 5 mm.

The disclosure further provides a method for dilating a stricture site in the body of a patient. The method may include inserting the dilation device into a stricture site of a patient, expanding the occlusion anchor expandable body at a point distal to the target stricture site, and expanding the dilation expandable body at the target dilation site. The method may further include pulling the occlusion anchor towards the stricture site to anchor the dilation expandable body. In an aspect, the method may include deflating the dilation expandable body. The method may further include additional expansion of the dilation expandable body.

In another aspect, the method of dilating a stricture site in a patient may include inserting the dilation device into a patient, expanding the occlusion anchor expandable body at the stricture site, and expanding the dilation expandable body at the stricture site. In an aspect, the method may include deflating the dilation expandable body and the occlusion anchor expandable body.

Additional aspects and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as variations of the disclosure and should not be construed as a complete recitation of the scope of the disclosure, wherein:

FIG. 6A is an illustration of the dilation device with a deflated occlusion anchor balloon and a deflated dilation balloon within a stricture site in one variation.

FIG. 6B is an illustration of the dilation device with an inflated occlusion anchor balloon and a deflated dilation balloon within a stricture site in one variation.

FIG. 6C is an illustration of the dilation device with an inflated occlusion anchor balloon and an inflated dilation balloon within a stricture site in one variation.

DETAILED DESCRIPTION

Figure 1:
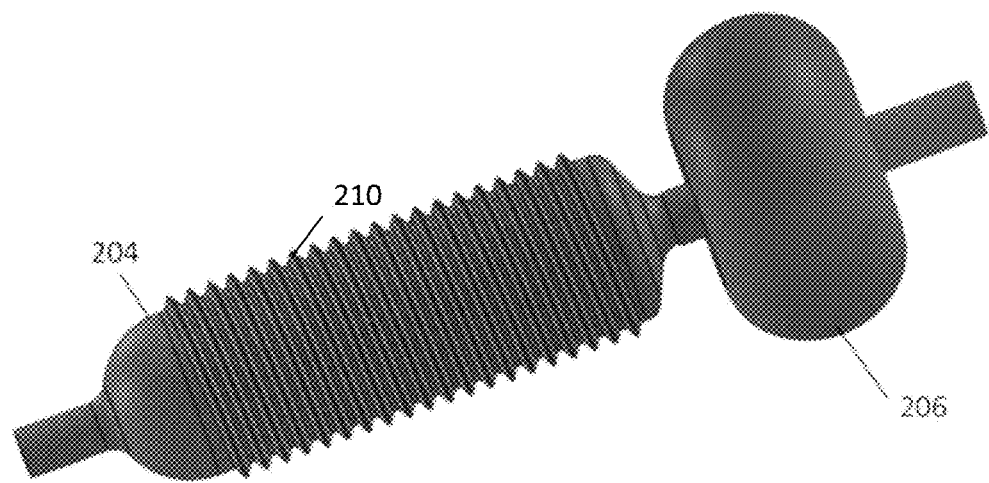
FIG. 1 is a side view showing a portion of a variation of the dilation device with the dilation balloon and occlusion anchor balloon separated by a small distance.

The disclosure may be understood by reference to the following detailed description, taken in conjunction with the drawings as described below. It is noted that, for purposes of illustrative clarity, certain elements in various drawings may not be drawn to scale.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, "substantially cylindrical" means that the object resembles a cylinder, but can have one or more deviations from a true cylinder. The terms "comprising," "including" and "having" are used interchangeably in this disclosure. The terms "comprising," "including" and "having" mean to include, but not necessarily be limited to the things so described.

The term "expandable body" may be used interchangeably with expandable dilation balloon and expandable occlusion anchor balloon.

Disclosed herein are systems, devices, and methods for dilation using a dilation device with at least two expandable bodies. For example, the dilation device may include a catheter body with an expandable dilation balloon and an expandable occlusion anchor balloon and a manifold for inflating the expandable bodies or injecting contrast dye. Standard, unanchored dilation balloons are typically longer than the stricture site to provide stability of the balloon in the stricture site when expanded at higher pressures. However, this leads to excess dilation of healthy tissue beyond the proximal and distal ends of the stricture site. Therefore, the present dilation device provides for a reduction in the excess dilation by reducing the length of the dilation balloon to be closer to the length of the actual stricture. However, in reducing the length of the dilation balloon, there is an increased likelihood that the dilation balloon will migrate or move within or out of the stricture site during expansion due to the high pressures in the balloon. Therefore, the dilation device may further include an occlusion anchor balloon to anchor the dilation balloon in place, such that any migration of the dilation balloon is minimized or eliminated. The benefits to the dilation device include the ability to reduce the length of the dilation balloon to reduce excess dilation; to reduce migration of the shorter dilation balloon through an occlusion anchor balloon with 1-2 bulbs; to deploy an occlusion anchor balloon with 2 bulbs at the proximal and distal ends of the stricture site such that the net treatment length of the dilation balloon is within the stricture site; to deploy the occlusion anchor balloon first, pull against the stricture, and seat the dilation balloon for optimal position and to eliminate migration; to create a wider range of inflation for the dilation balloon; to further reduce migration through ribbing; and to provide a flat surface on the proximal end of the dilation balloon to improve visualization.

Further provided herein are systems, devices, and methods for papillary/biliary dilation and stone removal using a dilation and extraction device. For example the dilation and extraction device may include a biliary catheter body with an expandable dilation balloon and an expandable occlusion/extraction balloon and a manifold for inflating the expandable bodies or injecting contrast dye. The dilation and extraction device provides a dual function in one device for both the dilation of an opening and the removal of an object to reduce the number of devices needed in an operation and reduce the length of time of such operation.

The expandable bodies may be first introduced in a non-expanded state into a patient using a dilation device and endoscope. The dilation device with expandable bodies may be negotiated in the non-expanded state to a target treatment site (i.e., stricture site, dilation site, or removal site). At least one expandable body may be expanded at or distal to the target treatment site into an expanded state. For example, the occlusion anchor balloon may be expanded at a point distal to the stricture site. The dilation device may then be pulled toward the stricture site such that the occlusion anchor balloon is anchored against the distal end of the stricture site and positions the dilation balloon within the stricture site. The dilation balloon may then be expanded to dilate the stricture site. In another example, the dilation balloon may be inside the occlusion anchor balloon such that both the occlusion anchor balloon and the dilation balloon may be expanded at the structure site. In some variations, the body of the occlusion anchor balloon may be within the stricture site while one or more bulbs of the occlusion anchor balloon may extend proximal or distal from the stricture site. In some examples, the bulbs may extend no more than 0.5-2 cm beyond the stricture site in the proximal and/or distal direction. Therefore, the body of the occlusion anchor balloon and the net treatment length of the dilation balloon may be completely within the stricture. In some examples, the dilation balloon may extend no more than 0-1 cm beyond the stricture site in the proximal and/or distal direction. This arrangement of the balloons, which allows for a shorter dilation balloon than typically used in dilation procedures, may minimize or reduce migration of the dilation balloon while also minimizing or reducing excess dilation beyond the stricture site. For example, the independent inflation of an occlusion anchor balloon with bulbs at the proximal and distal ends of the stricture site anchors the dilation balloon in the stricture site, such that once the anchor balloon is in place, the dilation balloon may be separately expanded to dilate the stricture with minimal or no migration of the dilation balloon, as compared to a standard, unanchored dilation balloon.

In one variation, both expandable bodies are deflated after the stricture site is expanded for removal of the dilation device. In another variation, at least one expandable body may remain expanded while withdrawing the dilation device from the dilation site. In one variation, an object is pulled along with the occlusion/extraction expandable body and removed from the biliary system. After dilation, the expandable bodies may return to the non-expanded state, and the dilation device and endoscope may be removed from the body.

The catheter may be over-the-wire, fixed wire, or short wire compatible. In one example, a guide wire may be extended from the endoscope and advanced through a stricture site. The catheter body coupled to the guide wire may follow the inserted guide wire through the opening and to a target site to be dilated. In additional examples, a wire core may be inside the catheter such that a guide wire is not needed. In other examples, a guide wire may exit the catheter at a point proximal to the expandable bodies. Contrast dye may be injected through a lumen of the catheter body using the manifold coupled to catheter body. In one variation, the dye may then exit the catheter body to assist a surgeon in locating the stricture site or dilation device or detecting an approximate location of an object to be removed. In another example, contrast dye may be combined with the fluid used to inflate the dilation expandable body. Alternatively, the dilation device may include a radiopaque ink or marker on at least a portion of an expandable body or catheter. The contrast dye or ink may be visible through a radioimaging device, for example, an x-ray machine, computer aided tomographic scanner, or other similar systems.

Figure 2:
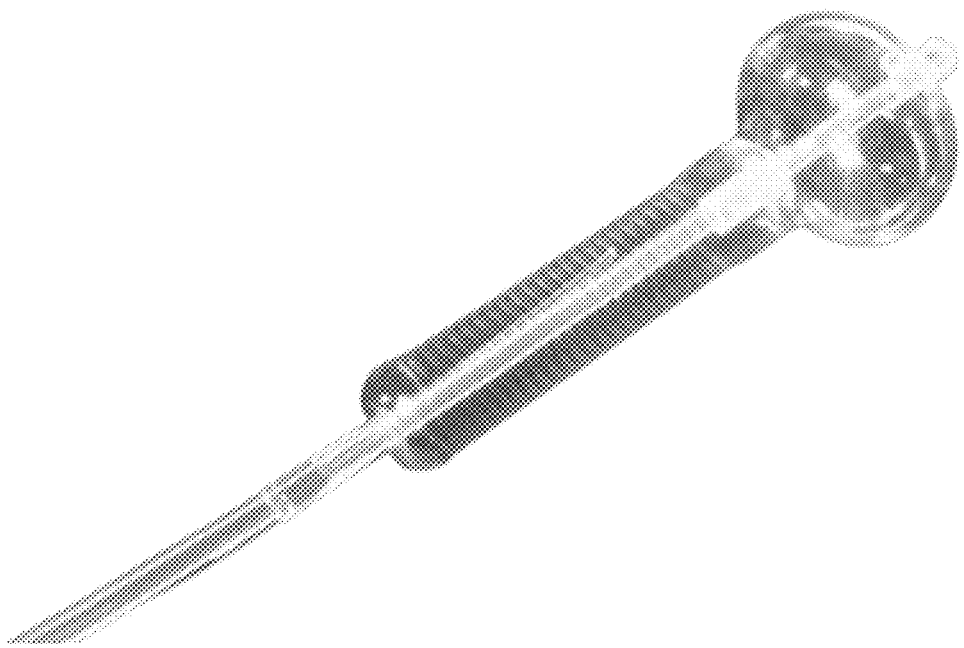
FIG. 2 is a perspective view of a variation of the dilation device with the dilation balloon and occlusion anchor balloon fused together.
Figure 7A:
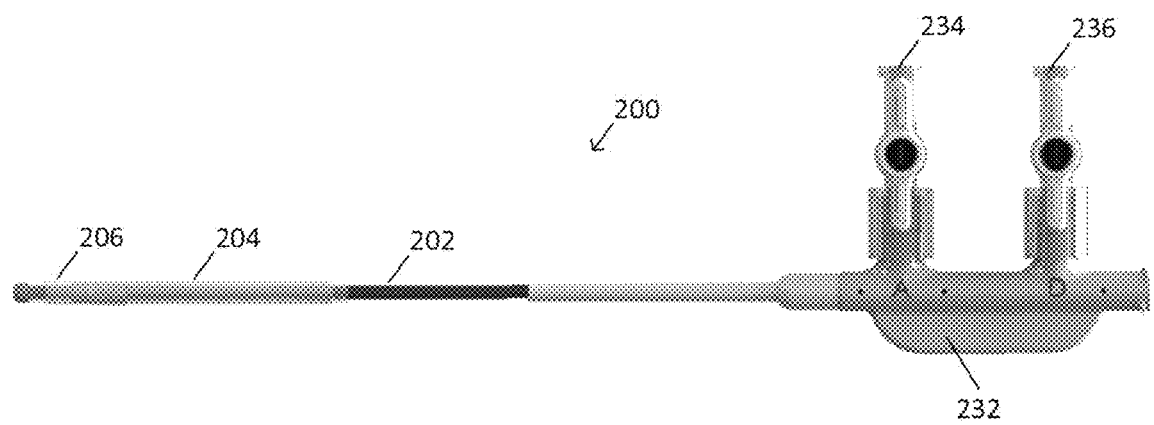
FIG. 7A is a side view of a variation of the dilation device with an occlusion anchor balloon over the dilation balloon in a deflated state.
Figure 7B:
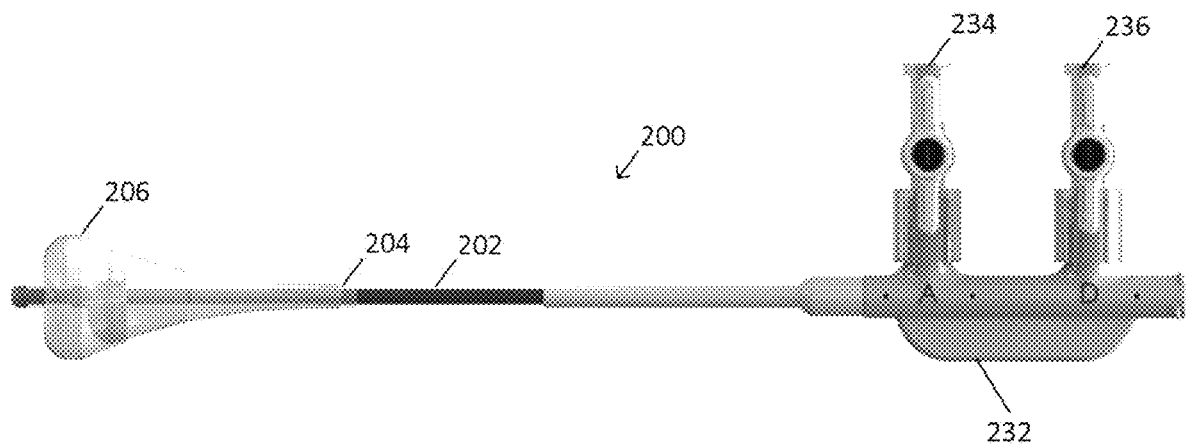
FIG. 7B is a side view of a variation of the dilation device with an occlusion anchor balloon over the dilation balloon, with the occlusion anchor balloon in the expanded state and the dilation balloon in the deflated state.
Figure 8A:
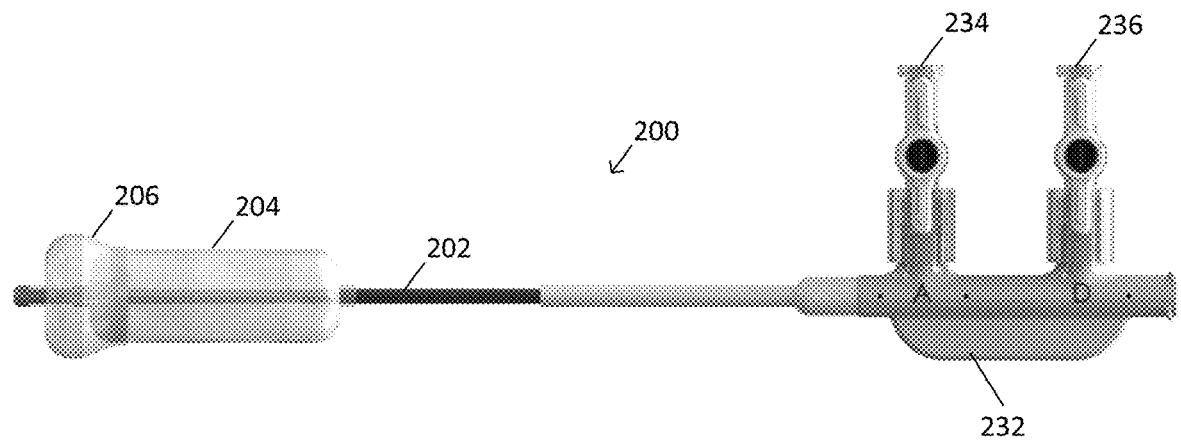
FIG. 8A is a side view of a variation of the dilation device with an occlusion anchor balloon over the dilation balloon, with the occlusion anchor balloon in the expanded state and the dilation balloon in the expanded state, where the occlusion anchor balloon has a diameter greater than the diameter of the dilation balloon.
Figure 8B:
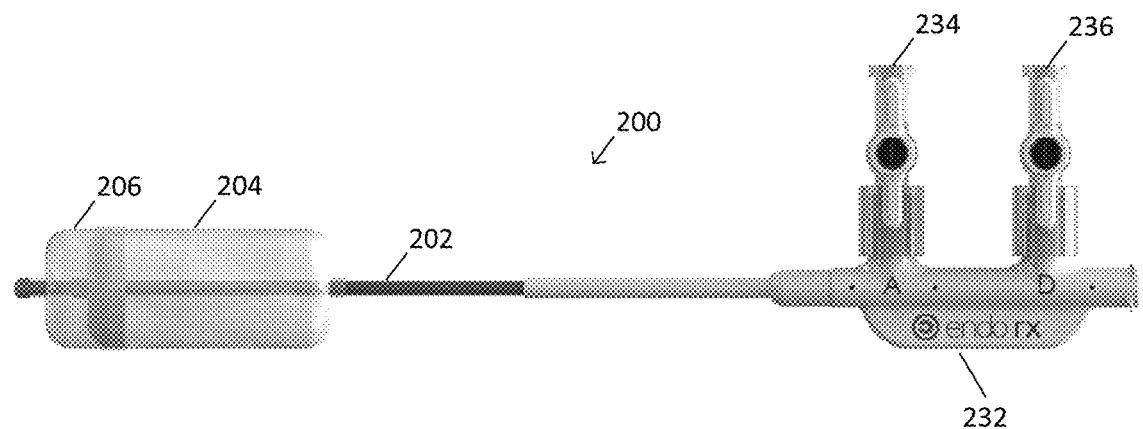
FIG. 8B is a side view of a variation of the dilation device with an occlusion anchor balloon over the dilation balloon, with the occlusion anchor balloon in the expanded state and the dilation balloon in the expanded state, where the occlusion anchor balloon has the same diameter as the dilation balloon.
Figure 9:
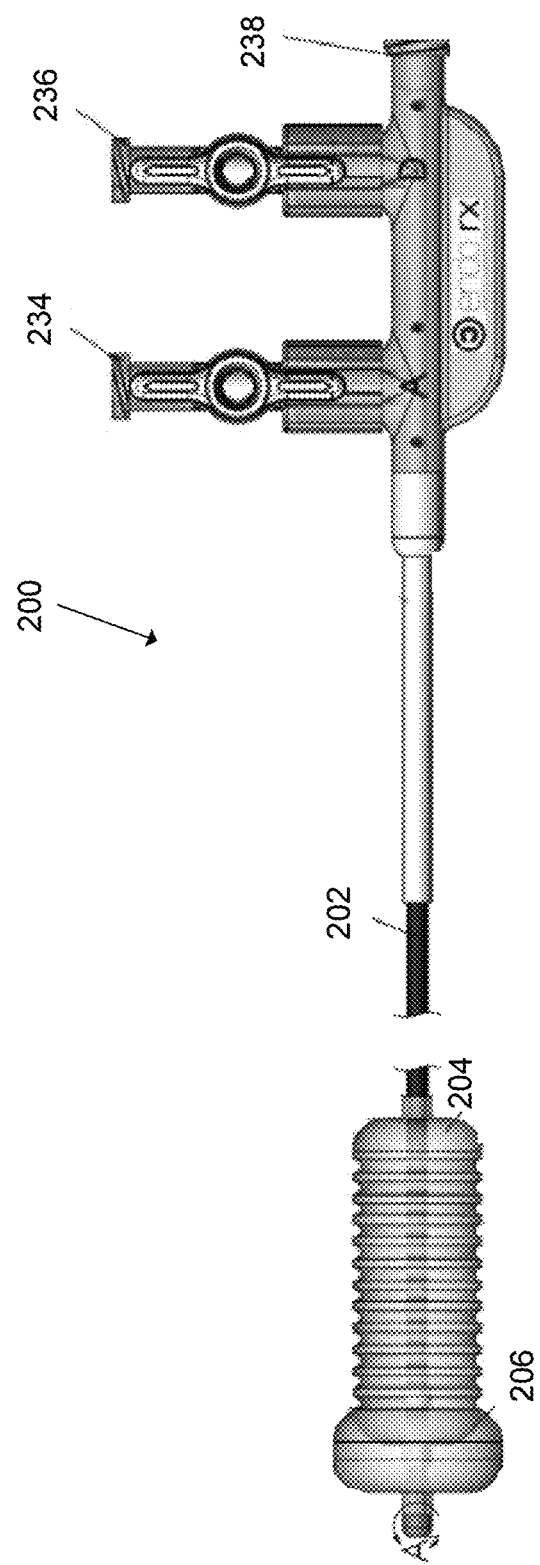
FIG. 9 is an illustration of a variation of the dilation device with the dilation balloon and occlusion anchor balloon welded together.

FIGS. 1, 3, 4, 8A, 8B, and 9 are side views and FIG. 2 is a perspective view of variations of the dilation device 200 with an expandable dilation balloon 204 in an expanded state and an occlusion anchor balloon 206 in an expanded state. FIG. 7A is a side view of a variation of the dilation device 200 with an expandable dilation balloon 204 in a deflated state and an occlusion anchor balloon 206 in a deflate state where the occlusion anchor balloon extends over the dilation balloon. FIG. 7B is a side view of the dilation device 200 with an expandable dilation balloon 204 in a deflated state and an occlusion anchor balloon 206 in an expanded state where the occlusion anchor balloon extends over the dilation balloon.

Figure 3:
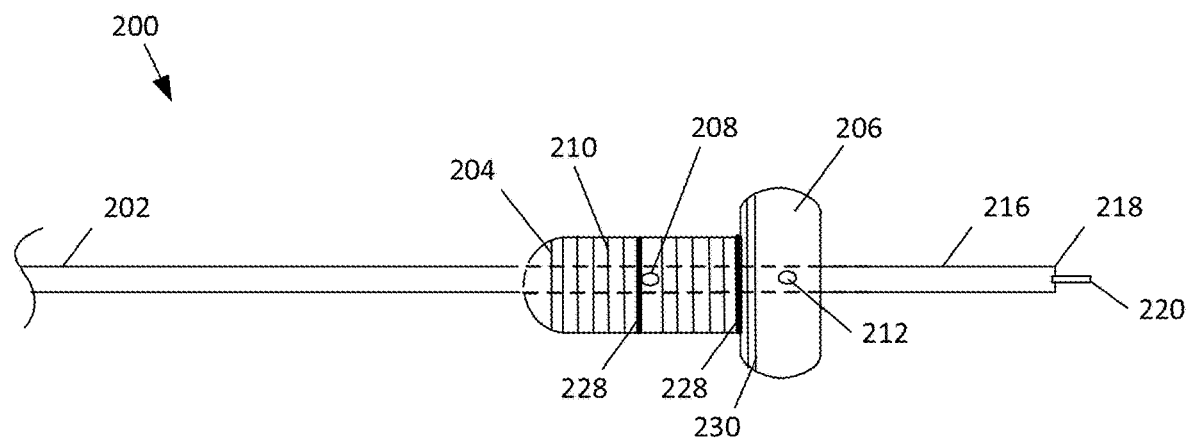
FIG. 3 is an illustration of a variation of the dilation device with the dilation balloon and occlusion anchor balloon fused together.
Figure 4:
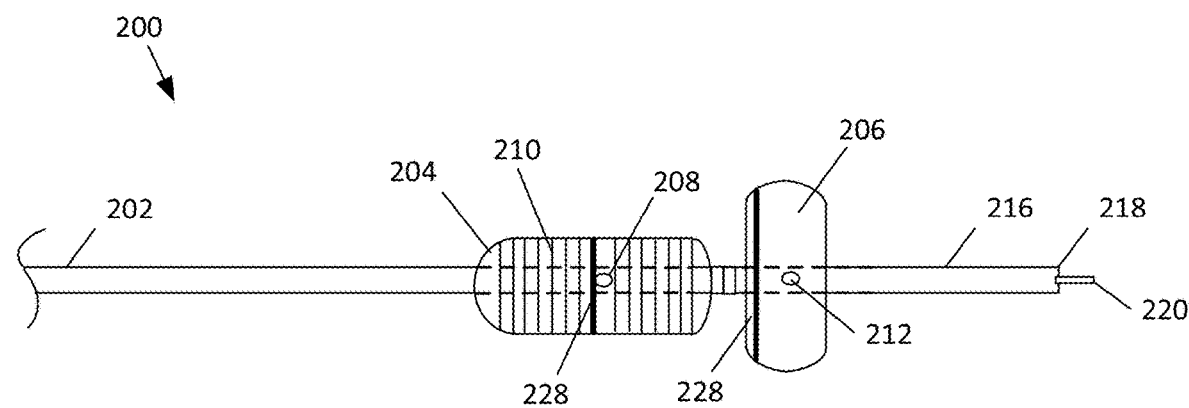
FIG. 4 is an illustration of a variation of the dilation device with the dilation balloon and occlusion anchor balloon separated by a small distance.
Figure 5A:
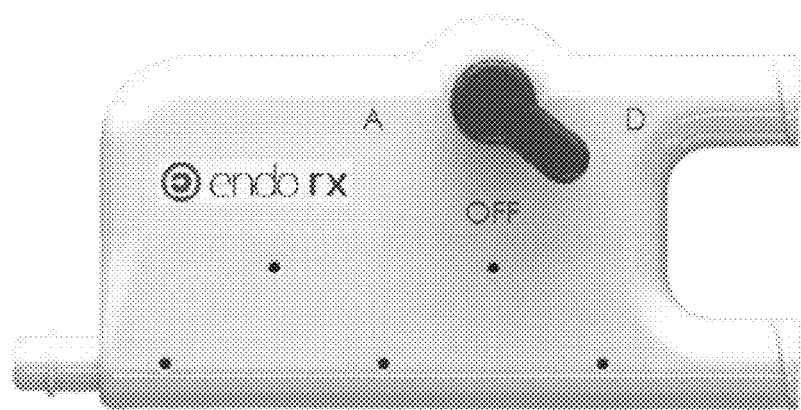
FIG. 5A is a side view of the manifold of the dilation device in one variation.
Figure 5B:
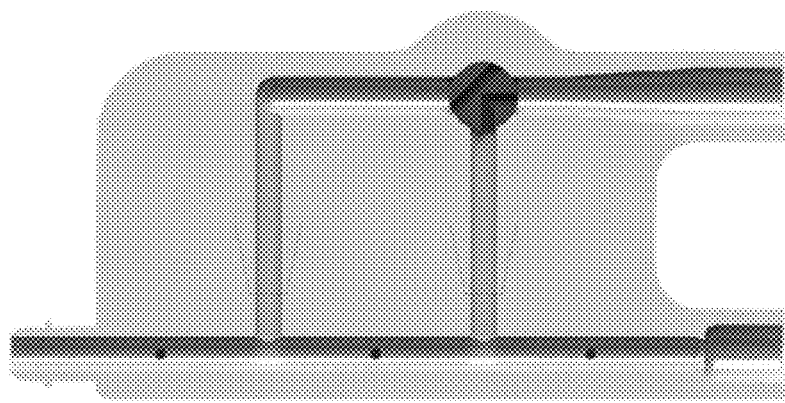
FIG. 5B is a cross-sectional view of the manifold of the dilation device in one variation.

The occlusion anchor balloon 206 may be separated by a distance from the dilation balloon 204, as seen in FIGS. 1 and 4, or may be externally connected to the dilation balloon 204, as seen in FIGS. 2, 3, and 7-9. The proximal end of the occlusion anchor balloon 206 may be connected at any point along the length of the dilation balloon 204, such that there may be overlap between the two balloons.

Figure 22:
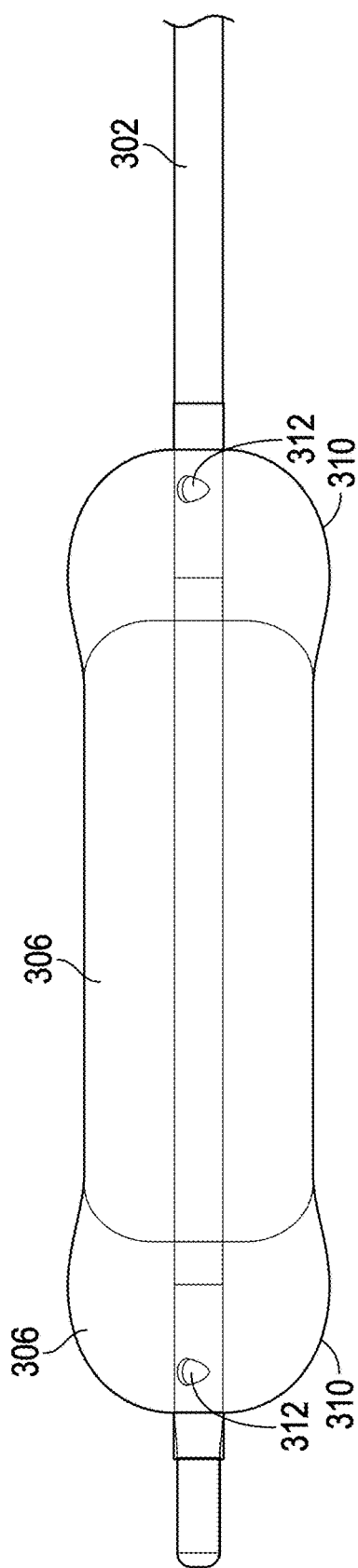
FIG. 22 is a side view of a variation of the dilation device with a dilation balloon inside an occlusion anchor balloon with two bulbs.
Figure 23:
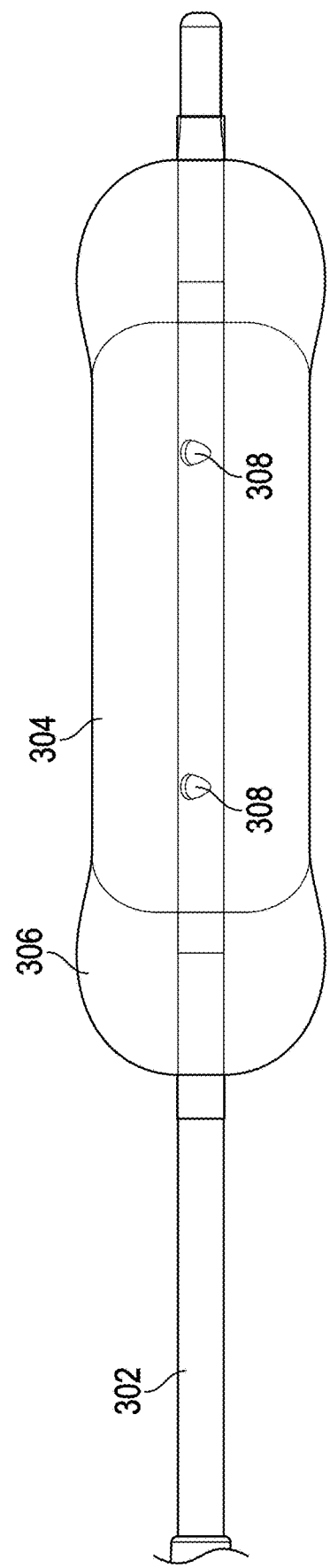
FIG. 23 is a side view of a variation of the dilation device with a dilation balloon inside an occlusion anchor balloon with two bulbs.
Figure 30:
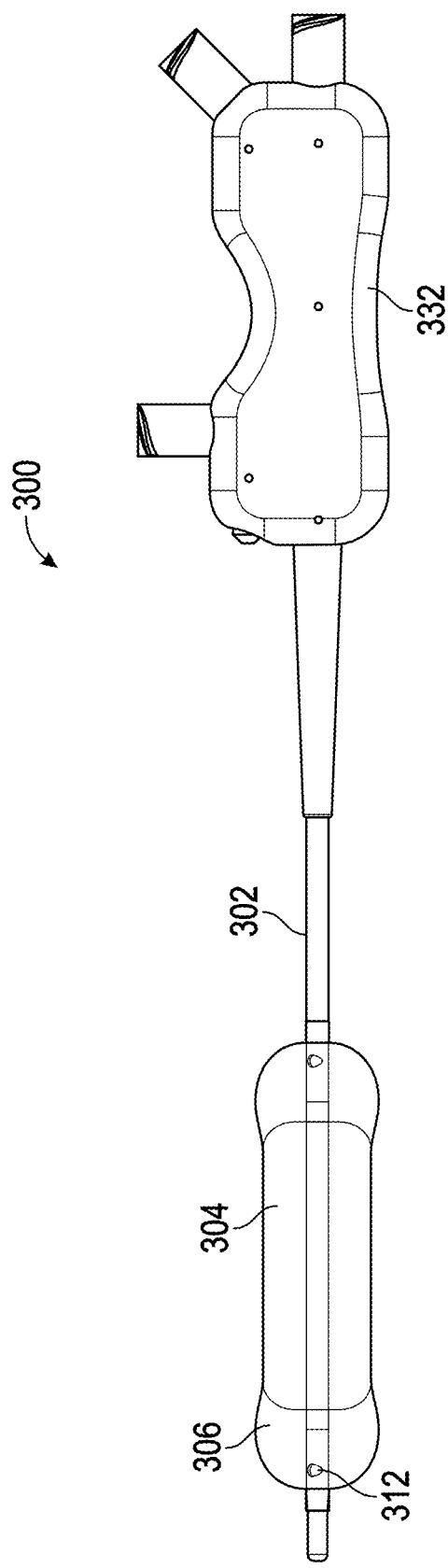
FIG. 30 is a side view of a variation of the dilation device.
Figure 31:
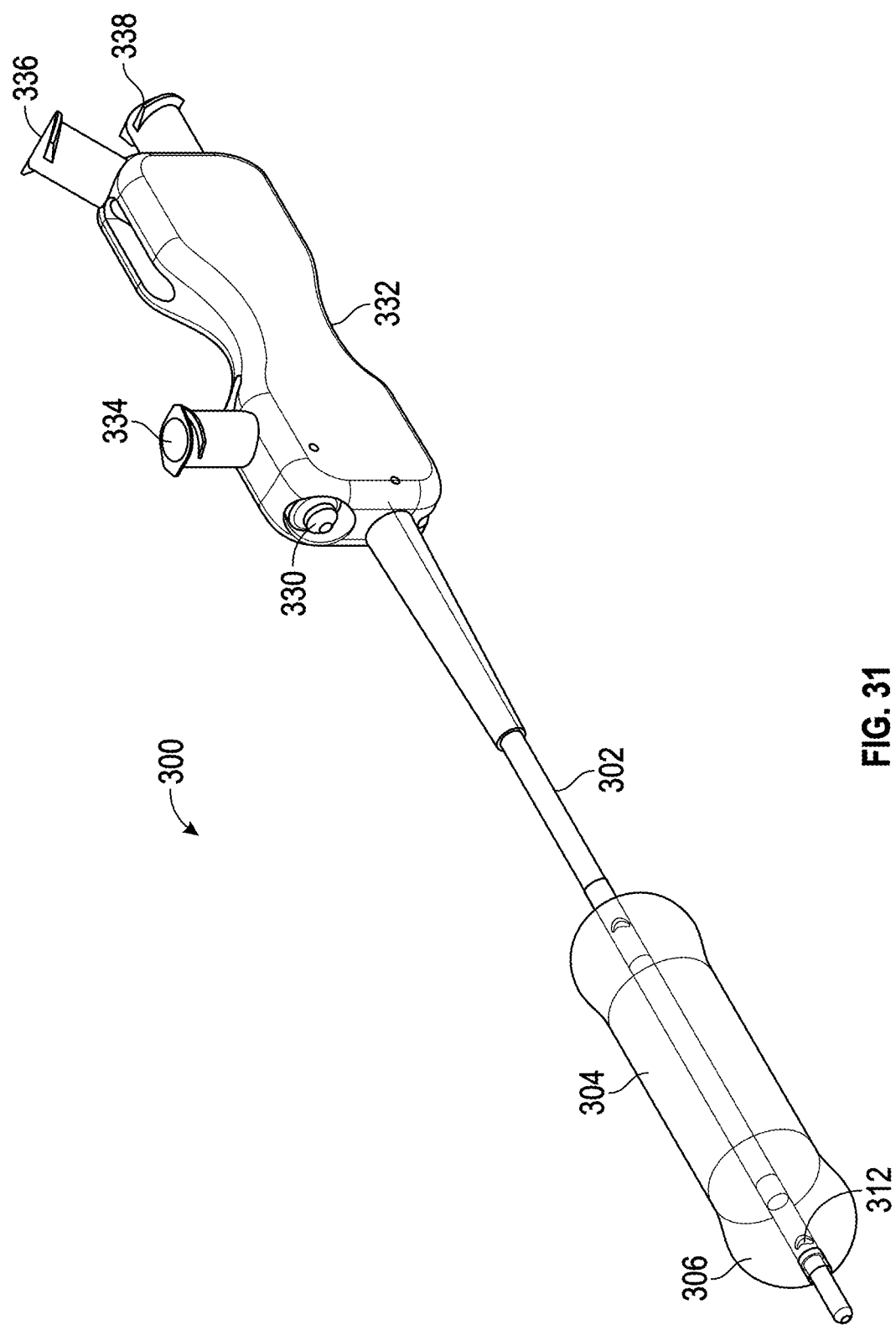
FIG. 31 is a perspective view of a variation of the dilation device.

FIGS. 22-23 and 30 are side view and FIG. 31 is a perspective view of variations of a dilation device 300 with a dilation balloon 304 in an expanded state and an occlusion anchor balloon 306 with two bulbs 310 in an expanded state, where the dilation balloon 304 is nested inside the body of the occlusion anchor balloon.

Figure 12:
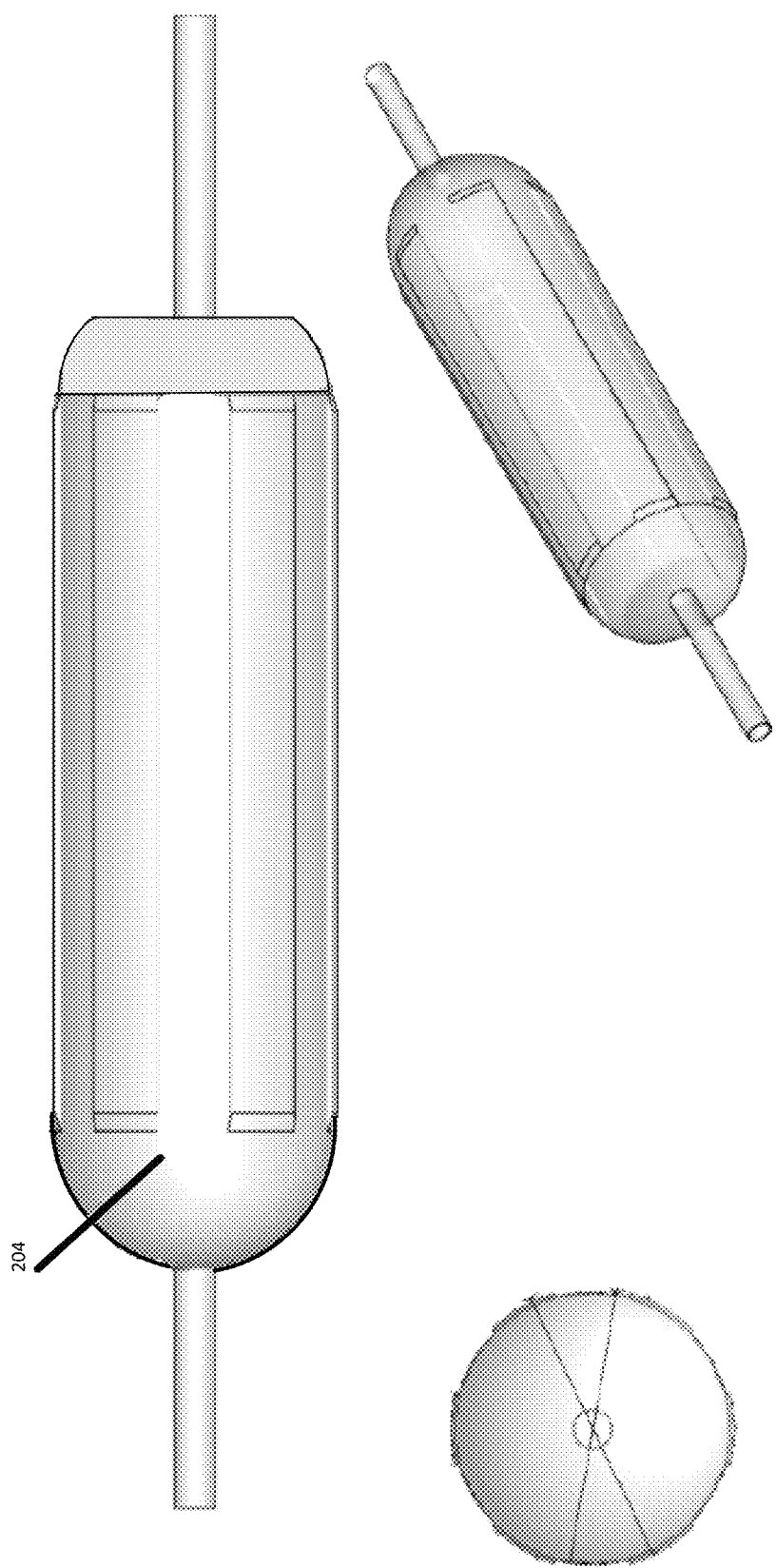
FIG. 12 is an illustration of the dilation balloon with longitudinal ridges in one variation.

The dilation balloon 204 and/or occlusion anchor balloon may have ribs 210 which provide friction at the stricture site to help prevent slippage of the dilation balloon 204 and/or occlusion anchor balloon during the dilation process. In some variations, the ribs 210 may be circumferential, as seen in FIGS. 1-4 and 9, or longitudinal, as seen in FIG. 12. In other variations, the dilation balloon 204 and/or occlusion anchor balloon may not include any ribs.

Figure 27:
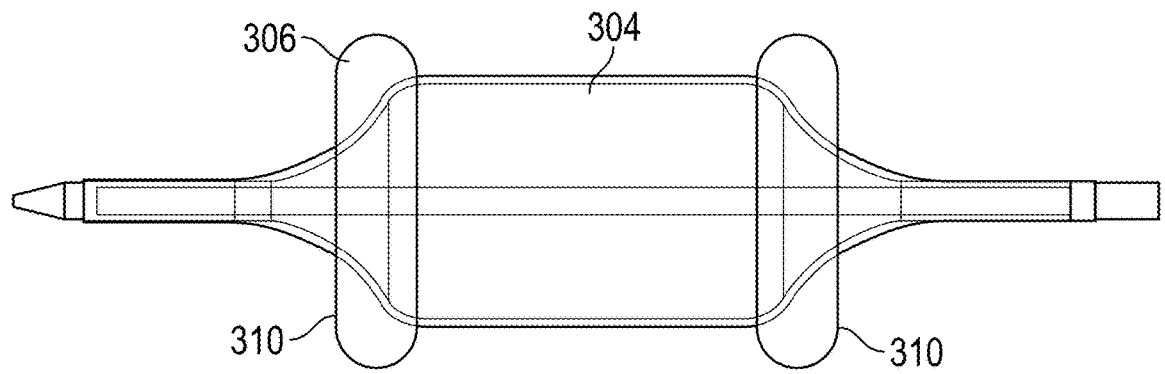
FIG. 27 is a side view of a variation of the dilation device with a dilation balloon inside an occlusion anchor balloon with two bulbs.

As seen in the figures, the expandable dilation balloon 204 and the occlusion anchor balloon 206 may be adjacent, connected, nested, overlapping, or separated by a distance in some variations. In a variation, the occlusion anchor balloon 206 overlaps at least a portion of the dilation balloon 204. In at least one variation, as seen in FIGS. 22, 23, and 27, the occlusion anchor balloon 306 surrounds the dilation balloon 304. Stated another way, the dilation balloon 304 may be inside the occlusion anchor balloon 206 such that the occlusion anchor balloon 206 provides anchoring on either side of the dilation balloon 204. FIGS. 30 and 31 show the dilation device 300 with nested dilation 304 and occlusion anchor balloons 306 on a catheter 302 connected to a manifold or handle 332.

As seen in FIGS. 3 and 4, the dilation device 200 comprises a catheter body 202 with at least two openings on its distal portion which are each in fluid communication with one of the lumen of the catheter body 202. The dilation balloon 204 surrounds at least one opening 208 on the catheter body 202 and the occlusion anchor balloon 206 surrounds at least one separate opening 212 on the catheter body 202. Therefore, the expandable bodies may be independently expanded and deflated and may use a different medium for expansion. In a variation, the occlusion anchor balloon is inflated by two openings in the catheter and the dilation balloon is inflated by two additional openings in the catheter.

Figure 13:
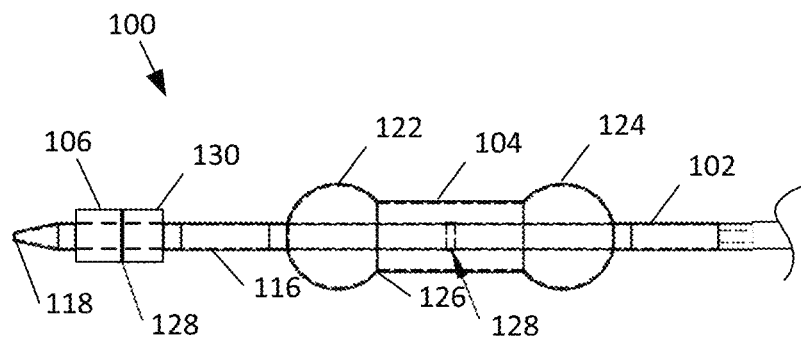
FIG. 13 is a side view of a variation of the dilation device with an extraction expandable body.
Figure 14:
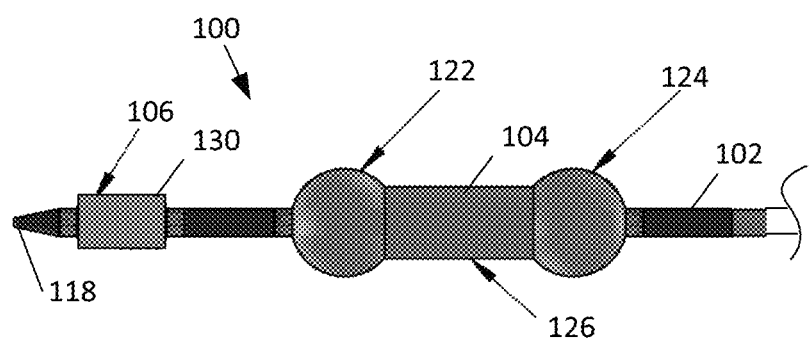
FIG. 14 is a side view of a variation of the dilation device with an extraction expandable body.
Figure 15:
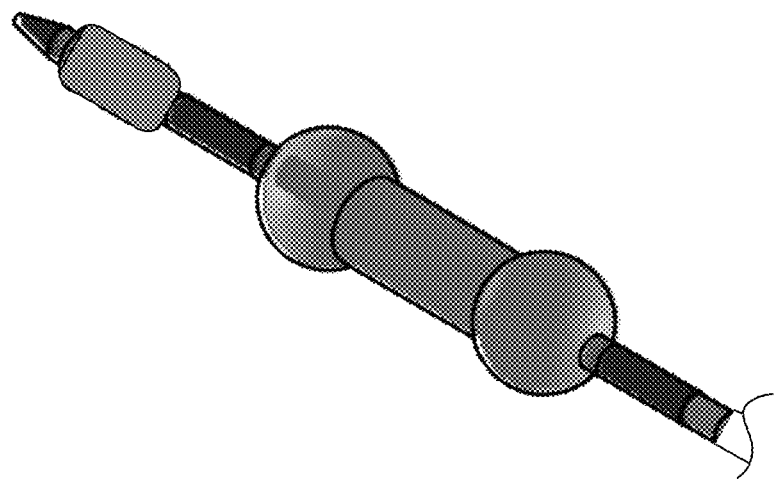
FIG. 15 is a perspective view of a variation of the dilation device with an extraction expandable body.

FIGS. 13 and 14 are side views and FIG. 15 is a perspective view of a variation of the dilation device 100 with an expandable dilation balloon 104 in the expanded state and expandable occlusion/extraction balloon 106 in the non-expanded state in one variation.

In some variations, the dilation balloon 104 may have at least one bulbous at the proximal portion 122, the distal portion 124, or at both ends to seat the dilation balloon 104 into the proper location in the stricture site. In other variations, the occlusion anchor balloon may have at least one bulb at the proximal portion, the distal portion, or at both ends to seat the dilation balloon into the proper location in the stricture site. For example, the bulb of the anchor balloon may aid in seating both the anchor balloon and the dilation balloon into the proper location in the lumen of the papillary opening or biliary duct such that it does not slip out of place when expanded. The occlusion anchor balloon may include ribs on a portion of the balloon to provide further resistance to migration of either balloon. In some variations, the occlusion anchor balloon may be used as an extraction balloon and may include ribs on a portion of the balloon to provide easier retrieval of the desired object.

Figure 16:
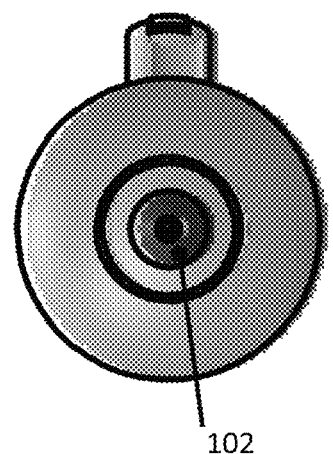
FIG. 16 is a view from the distal tip of the dilation device with an extraction expandable body in one variation.
Figure 17:
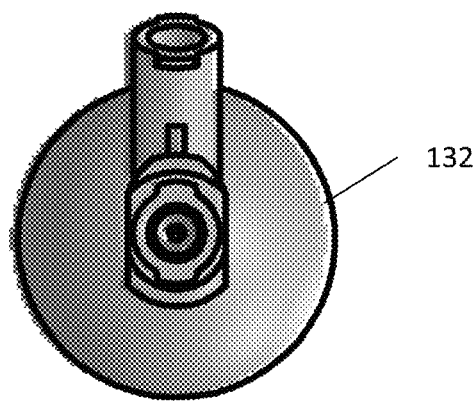
FIG. 17 is a view from the proximal end of the dilation device with an extraction expandable body in one variation.

FIG. 16 is a view from the distal tip of the dilation and extraction device in one variation. The catheter body 102 may include at least three lumina for the separate passage of air, fluid, dye, and/or a guide wire. FIG. 13 is a view from the proximal end of the dilation and extraction device. In this variation, the manifold 132 includes at least three openings that each fluidly connect to a separate lumen of the multi lumen catheter body 102.

Figure 18:
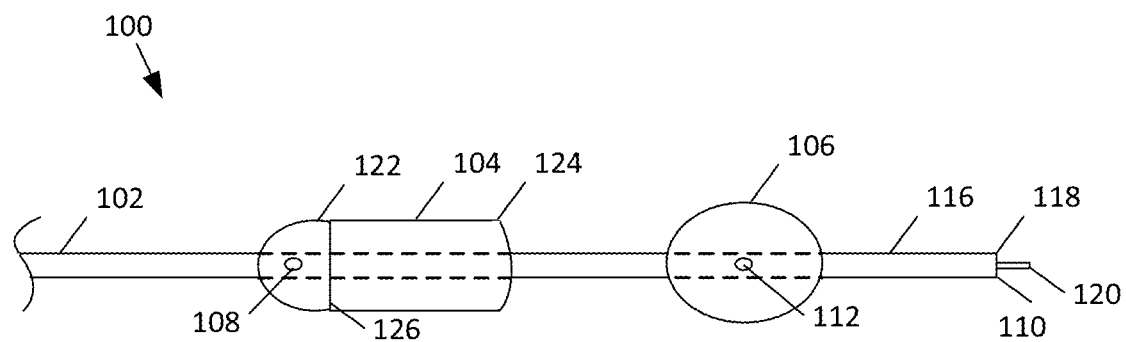
FIG. 18 is an illustration showing a portion of a variation of the dilation device with an extraction expandable body with a dye opening proximal to the extraction balloon.

FIG. 18 is an illustration of a portion of the dilation device 100 with an expandable dilation balloon 104 and expandable occlusion/extraction balloon 106 in the expanded state. The dilation device 100 comprises a catheter body 102 with at least two openings on its distal portion which are each in fluid communication with one of the at least three lumen of the catheter body 102. The dilation balloon 104 surrounds one opening on the catheter body 102 and the occlusion/extraction balloon 106 surrounds a separate opening on the catheter body 102. Therefore, the expandable bodies may be independently expanded and deflated and may use a different medium for expansion.

It will be appreciated by those skilled in the art that the expandable bodies may vary in size or shape. The dilation balloon and the occlusion anchor balloon may each have a different size and shape. In a variation, the volume of an expandable body may be increased through a compressible and/or incompressible fluid or air injected from the manifold through a lumen of the catheter body until the expandable body reaches a desired volume or diameter. The dimensions of the catheter body, such as diameter, length, or thickness may also vary. The lumina of the catheter body may also vary in cross-sectional shape, configuration, size, and/or number. The material of the expandable bodies may vary in compliance.

The dilation device, including the catheter body and expandable bodies, may be formed of a material which is flexible, deformable, and resistant to puncture. For example, thermoplastic polyurethane, a polyether block amide (Pebax®), a thermoplastic elastomer of flexible polyether and rigid polyamide (e.g., Pebax® 7233), a mixture of Pebax® and urethane, or a mixture of polyurethane and nylon may be used to fabricate the expandable bodies. In one variation, the dilation balloon may be formed from Pebax®. In another variation, the occlusion anchor balloon may be formed from Pebax®. In a variation, the catheter body may be formed from polyurethane. Non-limiting examples of polyurethane that may be used for the expandable bodies or catheter body include partially or fully thermoplastic polyurethane, an aromatic material based on isocyanates such as methylene diphenyl diisocyanate and/or related compounds, or an aliphatic thermoplastic polyurethane based on isocyanates such as methylene dicyclohexyl diisocyanate ($H_{12}$MDI). In a variation, the occlusion anchor balloon is more compliant than the dilation balloon.

Pebax®, polyurethane, Pebax®/urethane, or polyurethane/nylon expandable bodies may provide a benefit over standard balloons, in that they may be stronger, less likely to break or tear, less prone to leakage or separation from the catheter body, and less likely to cause an allergic reaction. In addition, Pebax®, polyurethane, Pebax®/urethane, or polyurethane/nylon expandable bodies can be made to expand to a wide range of inflation diameters, thus creating the ability to expand to most desired dilation diameters. Standard balloons are limited to smaller inflation ranges and are created in segmented inflation sizes, such as 8-12 mm and 12-15 mm, thus requiring the need to use multiple devices to treat patients with a need for a wide range of dilation diameters. A latex balloon that pops, leaks, or separates may require a new balloon to be inserted, whereas the present dilation device may provide dilation without needing to be replaced or reinserted. The compliance of the dilation device at a lower pressure may allow dilation of the stricture sites within the GI tract or biliary tract that were otherwise unobtainable by a single dilation balloon. The strength and dual purpose of the dilation and extraction device may allow dilation of the papillary opening and/or biliary ducts and retrieval of an object in a single attempt.

The disclosed device and method for dilation provide a simpler and more efficient way of dilating stricture sites throughout the GI tract. For example, the occlusion anchor balloon reduces or prevents migration of the dilation balloon in the stricture site, allowing for a shorter dilation balloon and reducing the likelihood of overdilation of areas not within the stricture site. In some variations, the dilation device may also be configured to remove stones in varying sized bile ducts. The dilation device may save time and resources during an operation and the device may be stronger and less prone to puncture, leakage, or popping.

It should be noted that the dilation device represents a single variation for dilation or a single variation for use with a stone removal procedure, and claimed subject matter is not limited to any particular variation. For example, a dilation device may be used in association with endoscopic devices and advanced into other body cavities, including but not limited to the esophagus, colon, papillary opening, or biliary ducts of a human patient, animal patient, or into a mechanical structure. Other variations may involve the use of other types of probing devices that may be used to dilate or retrieve objects in internal structures of living organisms and/or mechanical apparatuses, and the claimed subject matter is not limited in this respect.

Catheter Body

As illustrated in FIGS. 3 and 4, the dilation device 200 may include an elongated catheter body 202 having a proximal portion defining a catheter opening and a distal portion 216 defining a distal tip 218. As illustrated in FIG. 13, the dilation device 100 with an occlusion/extraction balloon may include an elongated catheter body 102 having a proximal portion 114 defining a catheter opening and a distal portion 116 defining a distal tip 118. As illustrated in FIGS. 7A-7B and 8A-8B, the catheter body 202 may attach to or extend through the length of a manifold, such that the catheter opening may be at the proximal end of the manifold. In addition, the catheter body 202 may include at least two lumina that extend longitudinally along the elongated catheter body 202. In one variation, the catheter body 202 includes three lumina. The at least two lumina have a proximal end in communication with the catheter opening and a distal end at the distal tip 218 of the catheter body 202. In a variation, the distal tip 218 of the catheter body 202 may be closed. In another variation, at least one of the distal ends of the at least two lumina may be closed at the distal tip 218 of the catheter body 202. In one variation, the catheter is an over-the-wire catheter and a guide wire 220 may extend through the distal tip 218 of the catheter body 202. In other variations, the catheter is a short wire catheter and the guide wire may exit the catheter at a point proximal to the expandable bodies. In additional variations, the catheter is a fixed wire catheter such that a separate guide wire is not needed.

As seen in FIGS. 3 and 4, the distal portion 216 of the catheter body 202 may include at least two openings 208 and 212 on the outer surface of the catheter body 202. In a variation, the distal portion of the catheter body may include 2 openings. In a variation, the distal portion of the catheter body may include 3 openings. In a variation, the distal portion of the catheter body may include 4 openings. In a variation, the distal portion of the catheter body may include 5 openings. For example, as seen in FIGS. 22 and 23, the distal portion of the catheter body may include 4 openings 308, 312. In at least one variation, the catheter body 202 may have a first opening, a second opening, and a third opening. Each opening may be connected to a separate lumen of the catheter body 202, such that a separate fluid may pass through each lumen and out a separate opening. In a variation, the first opening may be a dilation balloon opening 208 and the second opening may be an occlusion anchor balloon opening 212. As seen in FIG. 23, the catheter body may include two dilation balloon openings 308. In other variations, the catheter body may include one dilation balloon opening. As seen in FIG. 22, the catheter body may include two occlusion anchor balloon openings 312. For example, the catheter body may include an occlusion anchor balloon opening in the proximal bulb and the distal bulb of an occlusion anchor balloon having two bulbs. In some variations, the catheter body may include only one occlusion anchor balloon opening located at any point along the length of the occlusion anchor balloon. In some variations, the catheter body may include an opening for dye to be released. The first opening, the second opening, and/or the third opening may be in any order along the distal portion of the catheter body. In a variation, the dilation balloon opening 208 may be proximal to the occlusion anchor balloon opening 212. In another variation, the dye opening may be either proximal or distal to the occlusion anchor balloon opening 212. In some variations, the distal portion of the catheter body may have two dilation balloon openings between two occlusion anchor balloon openings. In other variations, the distal portion of the catheter body may not include an opening for dye.

The lumina of the catheter body 102, 202, 302 may allow for the passage of fluids, liquids, gases, dyes, gels, or solids through the lumina and optionally out the catheter body through one of the at least two openings on the catheter body or the distal tip of the catheter body. In a variation, a fluid or gas may pass through a lumen and exit through the occlusion anchor balloon opening(s) 212, 312 or the occlusion/extraction balloon opening 112 of the catheter body 102, 202, 302. In another variation, a fluid or gas may pass through a lumen and exit through the dilation balloon opening(s) 108, 208, 308 of the catheter body 202, 302. In yet another variation, a dye may pass through a lumen and exit through the guide wire or dye opening 110 of the catheter body 102.

The catheter body further includes at least two expandable bodies fused or welded to the catheter body. The at least two expandable bodies may be an expandable dilation balloon 204, 304 and an expandable occlusion anchor balloon 206.

In one variation, the occlusion anchor balloon is an occlusion/extraction balloon 106. In a variation, the dilation balloon may be fused to the catheter body covering the dilation balloon opening(s) such that the dilation balloon may be expanded by a gas or fluid passing through a lumen of the catheter body, out the dilation balloon opening(s), and into the lumen of the dilation balloon. In another variation, the occlusion anchor balloon may be fused to the catheter body covering the occlusion anchor balloon opening(s) such that the occlusion anchor balloon may be expanded by a fluid or gas passing through a lumen of the catheter body, out the occlusion anchor balloon opening(s), and into the lumen of the occlusion anchor balloon.

In a variation, contrast dye may be delivered through a lumen of the catheter body and exit through the guide wire or dye opening 110 to allow a surgeon to observe areas either proximal or distal to the extraction balloon 106. In another variation, the contrast dye may be mixed with the fluid (e.g. saline) used to expand the dilation balloon. The contrast dye may provide for observation of an object to be removed, as well as observing nearby structures, for example, a biliary tree, bile duct, pancreatic duct, cystic duct, common hepatic duct, or other structures that may be in fluid communication with the biliary duct. In some examples, the contrast dye may remain on one side of the extraction balloon 106 depending on the location of the guide wire or dye opening 110 on the catheter body 102 and if the extraction balloon 106 is expanded to the size of the biliary duct to form a temporary seal. In some variations, the dilation and extraction device 100 may be positioned without the use of a contrast dye.

The catheter body may be wire guided (over-the-wire), short wire compatible, or have a fixed wire. In some variations, a guide wire 120, 220 may extend through one lumen of the catheter body to guide the catheter body to the target treatment site. In one variation, the guide wire may exit the catheter body at the distal tip. The dilation device may be short wire or long wire compatible. In a variation, the guide wire may enter the device at the catheter opening at the manifold. In another variation, the guide wire may enter the catheter body at a location distal to the manifold. In another variation, the guide wire exits the catheter body at a location proximal to the distal end of the catheter body. In another variation, the wire may be integral to the catheter body.

The elongated catheter body may have a diameter between about 1 mm and about 5 mm. The catheter body may have a diameter of between about 1 mm and about 2 mm, between about 1.5 mm and about 2.5 mm, between about 2 mm and about 3 mm, between about 2.5 mm and about 3.5 mm, between about 3 mm and about 4 mm, between about 3.5 mm and about 4.5 mm, and between about 4 mm and about 5 mm. In other variations, the catheter body size may range from about 3 French to about 15 French, from about 3 French to about 7 French, from about 5 French to about 9 French, from about 7 French to about 11 French, from about 9 French to about 13 French, and from about 11 French to about 15 French. In one variation, the catheter body may be a 7 French catheter, or about 2.33 mm in diameter and about 7.33 mm in circumference. In another variation, the catheter body may have a minimum internal diameter of about 0.41 inches. In various variations, the at least two lumina within the catheter body may each have a diameter between about 0.25 mm and about 1.5 mm, from about 0.25 mm to about 0.75 mm, from about 0.5 mm to about 1 mm, from about 0.75 mm to about 1.25 mm, and from about 1 mm to about 1.5 mm.

The catheter body may have a length ranging from about 180 cm to about 200 cm, from about 190 cm to about 210 cm, from about 200 cm to about 220 cm, from about 210 cm to about 230 cm, from about 220 cm to about 240 cm, and from about 230 cm to about 250 cm. In one variation, the catheter body has a length of 210 cm. In another variation, the catheter body has a working length of about 190 cm±3 cm and an overall length of about 195 cm±3 cm. The lumina may have varying cross-sectional shapes and diameters and may vary independently. In a variation, the cross-section of the lumina includes, but is not limited to circular, elliptical, or irregular. The catheter body may be made of polyurethane or any material capable of being inserted into the body. In a variation, the catheter body may have a stiffness greater than the catheter of a common balloon catheter. The increased stiffness may reduce the deformity of the device after multiple uses and provide improved resistance to kinking.

The catheter body of the dilation device is configured to fit into the working channel of an endoscope or other device such as a sigmoidoscopy device, colonoscopy device or other instrument with a working channel. The endoscope may include a camera on its distal end to help navigate the endoscope through the patient's body. In a variation, the camera may be used to confirm the endoscope is in the proper location prior to deploying the dilation device. In a variation, the proximal end of the dilation balloon and/or the occlusion anchor balloon may be shaped to allow the endoscope camera to be placed up against the balloon to allow a user to see through the dilation balloon and/or the occlusion anchor balloon. The catheter body may be inserted through a working channel of the endoscope. The catheter body may then exit the endoscope to the target area. In a variation, a guide wire may extend through the endoscope. The guide wire may be coupled to the catheter body through one lumen of the catheter body or be integral with the catheter body and aid the catheter body in navigating to the target site.

Expandable Bodies

In various variations, the dilation device includes at least two expandable bodies coupled to the catheter body. The expandable bodies are configured to be in an expanded or non-expanded form. FIGS. 1-4, 8A-8B, 19-27, 30-31, and 32D illustrate variations of the expandable bodies in an expanded state. FIGS. 7A, 7B, 32A, 32B, and 32C illustrate variations of the expandable bodies in a non-expanded or partially expanded state. FIGS. 13-15 illustrate one expandable body in an expanded state and the other expandable body in a non-expanded state. FIG. 18 illustrates the expandable bodies in an expanded state. The expandable bodies may have a single-layered or multi-layered construction. The expandable bodies may be formed using extrusion and an SLA mold to achieve the desired shape.

In a variation, the at least two expandable bodies are an expandable dilation balloon 204, 304 and an expandable occlusion anchor balloon 206, 306. In another variation, the at least two expandable bodies are an expandable dilation balloon 104 and an expandable occlusion/extraction balloon 106. The two expandable bodies may be separate or joined together by welding. In an example, a proximal portion of the occlusion anchor balloon may be attached to or welded over a distal portion of the dilation balloon. In one variation, the occlusion anchor balloon 206 includes "legs" or extensions that extend over the dilation balloon 204, as seen in FIGS. 7A-8B, to attach the occlusion anchor balloon to the dilation balloon. In another variation, the occlusion anchor balloon 306 may completely surround the dilation balloon 304, such that the dilation balloon is nested in the occlusion anchor balloon, as seen in FIGS. 22-23, 27, 30, and 31. In this variation, the occlusion anchor balloon and dilation balloon may be attached or welded together at multiple points along the length of the balloons.

The occlusion anchor balloon and the dilation balloon may be attached to each other through laser welding. The occlusion anchor balloon and the dilation balloon may be separately attached to the catheter body. The expandable bodies may be coupled to the catheter body using a thermoplastic welding process. This process may allow the expandable bodies to maintain pressure when an expanded state and reduce the likelihood of the expandable body separating from the catheter body by allowing the expandable body to withstand internal pressures when in the expanded state. The expandable bodies may be inflated with air, water, saline, or saline with diluted contrast.

Dilation Balloon

The dilation balloon is a high pressure expandable body. The dilation balloon may be made of Pebax® or polyurethane and may be thermo welded around the circumference of the catheter body in at least two locations. In some variations, the dilation balloon may include a radiopaque ink within the balloon composite or on the surface of the balloon.

The lumen of the dilation balloon is in fluid communication with at least one lumen of the catheter body through at least one dilation balloon opening in the catheter body. The dilation balloon is configured to dilate a stricture site in the GI tract or biliary tract with a fluid or gas though the dilation balloon opening. For example, the stricture site may be the esophagus, the colon, a papillary opening, or a biliary duct upon expansion. In one variation, the dilation balloon may be configured to dilate a papillary opening or a biliary duct upon expansion with a fluid or gas though the dilation balloon opening. The dilation balloon may be a pressure rated balloon. In a variation, the dilation balloon may be a controlled radial expansion balloon that is pressure rated to atmospheres for dilation. In this variation, the dilation balloon may produce at least two distinct diameters at at least two separate pressures during dilation. In one variation, the dilation balloon may produce at least three distinct diameters at at least three separate pressures during dilation. A pressure gun or inflator may be used to inflate the dilation balloon to the desired diameter. In a variation, the dilation balloon may be inflated with a fluid without the need for contrast, such as water or saline. In another variation, saline with diluted contrast may be delivered from the pressure gun or inflator to inflate the dilation balloon. In yet another variation, a pressure gun or inflator may not be needed to inflate the dilation balloon.

The diameter of the dilation balloon 204 may range from about 0.5 mm to about 25 mm. In various variation, the body of the expandable dilation balloon may be inflated to a diameter of at least 0.5 mm, at least 1 mm, at least 2 mm, at least 3 mm, at least 4 mm, at least 5 mm, at least 6 mm, at least 7 mm, at least 8 mm, at least 9 mm, at least 10 mm, at least 11 mm, at least 12 mm, at least 13 mm, at least 14 mm, at least 15 mm, at least 16 mm, at least 17 mm, at least 18 mm, at least 19 mm, at least 20 mm, or at least 25 mm. In some variations, the dilation balloon may have a dilation range of at least 3 mm. In a variation, the dilation balloon may have a dilation range of at least 4 mm. In additional variations the dilation balloon may have a dilation range of at least 5 mm. In some variations, the dilation balloon may have an inflation range of 3 mm to 5 mm. In other variations, the dilation balloon may dilate in the range of from 3 mm to 10 mm, 5 mm to 10 mm, 6 mm to 12 mm, 8 mm to 15 mm, from 7 mm to 10 mm, from 8 mm to 11 mm, from 9 mm to 12 mm, 10 mm to 15 mm, 12 mm to 15 mm, 15 mm to 20 mm, 20 mm to 25 mm, or 15 mm to 25 mm. The dilation balloon may be inflated to a range of diameters that may be incremented by 1 mm. For example, the dilation balloon may have a starting diameter of 15 mm and a final diameter of 20 mm or a diameter between 15 and 20 mm with 1 mm increments. In a variation, the dilation balloon may have 2, 3, 4, 5, 6, 7, 8, 9, or 10 distinct diameters within the expansion range. In one variation, the dilation balloon may have dilation levels of 5 mm, 6 mm, 7 mm, 8 mm, 9 mm, and/or 10 mm. In one variation, the dilation balloon may have dilation levels of 10 mm, 11 mm, 12 mm, 13 mm, 14 mm, and/or 15 mm. In one variation, the dilation balloon may have dilation levels of 15 mm, 16 mm, 17 mm, 18 mm, 19 mm, and/or 20 mm. In one variation, the dilation balloon may have four dilation levels of 9 mm, 10 mm, 11 mm, and 12 mm. In another variation, the dilation balloon may have four dilation levels of 6 mm, 12 mm, 15 mm, and 20 mm. In other aspects, the dilation balloon may have two dilation levels, for example 6 mm and 12 mm, or 12 mm and 20 mm.

The dilation balloon may be expanded through the injection of a fluid, such as saline, into the dilation balloon. In some examples, the dilation balloon is filled using an inflator, optionally connected to a stop cock, on a port on the manifold of the dilation device.

The dilation balloon may have an internal pressure that corresponds to its dilation diameter. The pressure may be incremented by a set amount to increase the diameter of the dilation balloon by a set amount. This allows the user to set the dilation balloon to a known diameter by knowing the pressure within the balloon. For example, the pressure increments within the balloon may correlate to specific increments in the diameter of the dilation balloon.

The dilation balloon may have a pressure range of up to 0.5 at, up to 1 atm, up to 2 atm, up to 3 atm, up to 4 atm, up to 5 atm, up to 6 atm, up to 7 atm, up to 8 atm, or up to 10 atm. In some variations, an increase in internal pressure of 0.5 atm results in a 1 mm increase in diameter of the dilation balloon. In another variation, an increment in pressure of 1 atm may correspond to an increment of 1 mm in the dilation balloon diameter. In another variation, an increment in pressure of 1.5 atm may correspond to an increment of 1 mm in the dilation balloon diameter. In other variations, an increase in pressure of 0.2 atm results in an increase in a 1 mm increase in diameter of the dilation balloon. In a variation, an increment of 1 mm in diameter of the dilation balloon may correspond to an increment of 0.2 atm to 0.5 atm.

In some examples, a 0.5 atm pressure in the dilation balloon corresponds to a diameter of 15 mm, a 1 atm pressure in the dilation balloon corresponds to a diameter of 16 mm, a 1.5 atm pressure in the dilation balloon corresponds to a diameter of 17 mm, a 2 atm pressure in the dilation balloon corresponds to a diameter of 18 mm, a 2.5 atm pressure in the dilation balloon corresponds to a diameter of 19 mm, a 3 atm pressure in the dilation balloon corresponds to a diameter of 20 mm, a 3.2 atm pressure in the dilation balloon corresponds to a diameter of 21 mm, a 3.4 atm pressure in the dilation balloon corresponds to a diameter of 22 mm, a 3.6 atm pressure in the dilation balloon corresponds to a diameter of 23 mm, a 3.8 atm pressure in the dilation balloon corresponds to a diameter of 24 mm, and a 4 atm pressure in the dilation balloon corresponds to a diameter of 25 mm. In a variation, the dilation balloon may have pressure/diameter correlation as indicated in Table 1 below. In some examples, a dilation balloon having a pressure/diameter correlation similar to Table 1 may be used where lower pressures may be sufficient for treatment. For example, this may include, but is not limited to papillary dilation.

TABLE 1

Example Pressure/Diameter Correlation

| | Pressure Atm | Balloon Diameter |
|---|---|---|
| Nominal Pressure | 0.5 | 15.00 |
| | 1 | 16.00 |
| | 1.5 | 17.00 |
| | 2 | 18.00 |
| | 2.5 | 19.00 |
| Rated Pressure | 3 | 20.00 |
| | 3.2 | 21.00 |
| | 3.4 | 22.00 |
| | 3.6 | 23.00 |
| | 3.8 | 24.00 |
| | 4 | 25.00 |

In another example, the dilation balloon may have a pressure/diameter correlation as indicated in Table 2 below. In some examples, a dilation balloon having a pressure/diameter correlation similar to Table 2 may be used where higher pressures may be required for treatment. For example, this may include, but is not limited to gastrointestinal luminal dilation or esophageal dilation.

TABLE 2

Example Pressure/Diameter Correlation

| ATM | Outer Diameter |
|---|---|
| 0.8 | 15.21 |
| 1 | 15.44 |
| 1.5 | 15.53 |
| 2 | 16 |
| 2.5 | 16.3 |
| 3 | 16.7 |
| 4 | 17.3 |
| 4.5 | 17.6 |
| 5 | 17.9 |
| 5.5 | 18.1 |
| 6 | 18.6 |
| 6.5 | 18.85 |
| 7 | 19 |
| 7.5 | 19.7 |
| 8 | 20 |
| 8.5 | 20.47 |

The dilation balloon may be inserted into a stricture site in the non-expanded state and then expanded for dilation of the stricture site. The dilation balloon may have a length ranging from at least 2 cm to at least 5.5 cm. In a variation, the dilation balloon has a length of 2 cm or less. In a variation, the dilation balloon has a length of up to 3 cm. In a variation, the dilation balloon has a length of up to 4 cm. In a variation, the dilation balloon has a length of up to 5 cm. In another aspect, the dilation balloon has a length of 4 cm±0.5 cm. The dilation balloon may have a net treatment length that is shorter than the total length of the dilation balloon. The net treatment length is the length of the dilation balloon which contacts and dilates the stricture site. In a variation, the dilation balloon has a net treatment length of less than or equal to 2 cm. In a variation, the dilation balloon has a net treatment length of less than or equal to 3 cm. In a variation, the dilation balloon has a net treatment length of less than or equal to 4 cm. In a variation, the dilation balloon has a net treatment length of less than or equal to 5 cm. The length of the dilation balloon and/or net treatment length may be determined by the target area or stricture site. For example, the dilation balloon may have a net treatment length approximately the same length of the stricture site. In a variation, the length of the dilation balloon and/or the net treatment length being close to the length of the stricture site reduces or prevents excess dilations in areas outside the stricture site. This may eliminate unnecessary dilation of healthy tissue. In some examples, the dilation balloon may not extend beyond the stricture site in the proximal and distal directions. In some examples, the dilation balloon may extend up to 0.5 cm beyond the stricture site in the proximal and distal direction. In other examples, the dilation balloon may extend up to 1 cm beyond the stricture site in the proximal and distal direction. In other examples, the dilation balloon may extend up to 1.5 cm beyond the stricture site in the proximal and distal direction. In other examples, the dilation balloon may extend up to 2 cm beyond the stricture site in the proximal and distal direction. The use of the occlusion anchor balloon allows for the length of the dilation balloon to be less than traditional dilation balloons because it anchors the dilation balloon in the proper location and reduces or eliminates migration of the dilation balloon during dilation.

The dilation balloon may be of a size that it can also provide dilation of biliary ducts. For example, a dilation balloon with a length of greater than 2 cm to less than 4 cm for papillary dilation is advantageous over the current dilation balloons that either have a length of 4 cm, which is unnecessarily long for papillary dilation, or a length of 2 cm, which is too short for papillary dilation and may create a torque on the catheter and cause the balloon to pop out of the papillary opening. Using current methods, if a narrowing of a biliary duct was observed during a stone extraction process and dilation was desired to be done at that time, the extraction balloon would have to be removed and a separate dilation balloon inserted. In many cases, this would be a different dilation balloon that what currently is used for papillary dilation because the size of the biliary ducts is smaller in comparison to the papillary opening. However, the dilation balloon has a length and diameter that may be used for both papillary dilation and biliary duct dilation, therefore obviating the need for separate devices for different types of dilation. Moreover, as seen in FIGS. 13-15, the dilation and extraction device 100 includes both a dilation balloon 104 and an occlusion/extraction balloon 106, thus the device 100 also eliminates the need to switch between separate devices for dilation and retrieval/extraction of objects.

Figure 10:
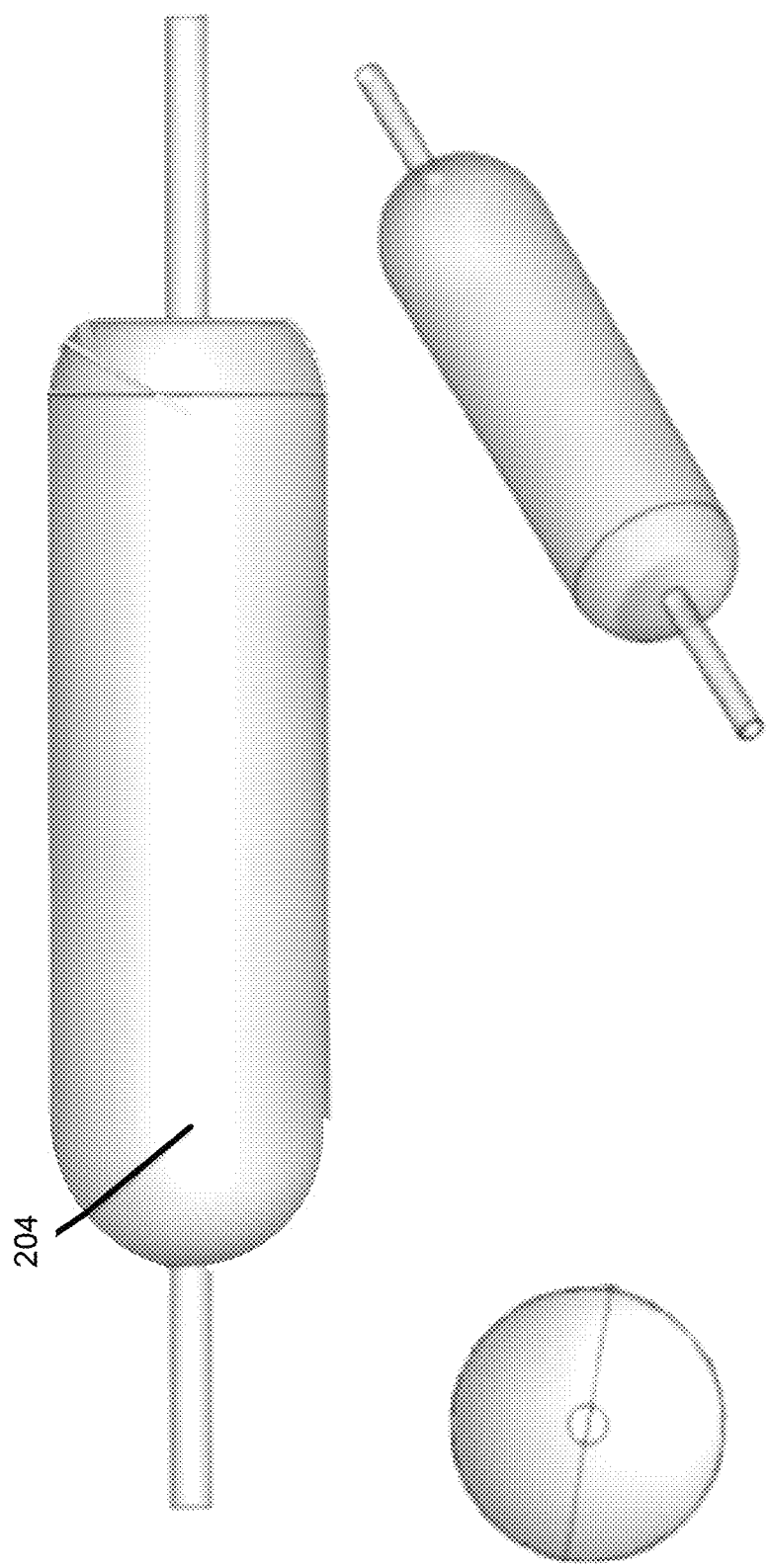
FIG. 10 is an illustration of the dilation balloon with a flat proximal end in one variation.
Figure 11:
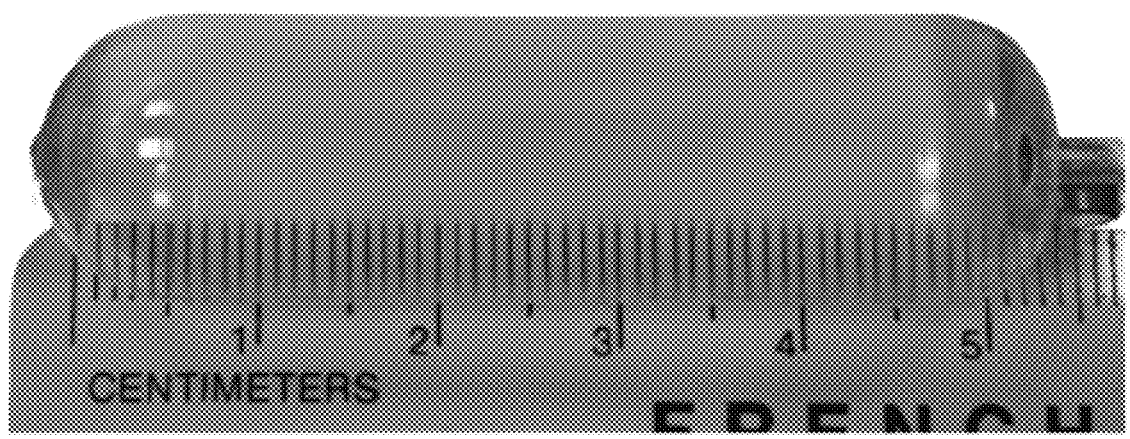
FIG. 11 is a photograph of an inflated dilation balloon without ribbing in one variation.
Figure 21:
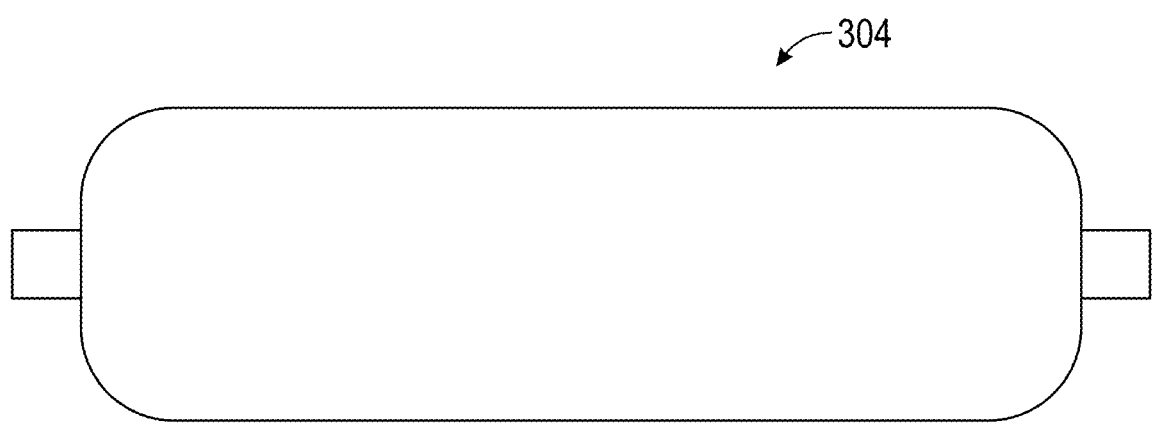
FIG. 21 is a side view of a variation of a dilation balloon.
Figure 24:
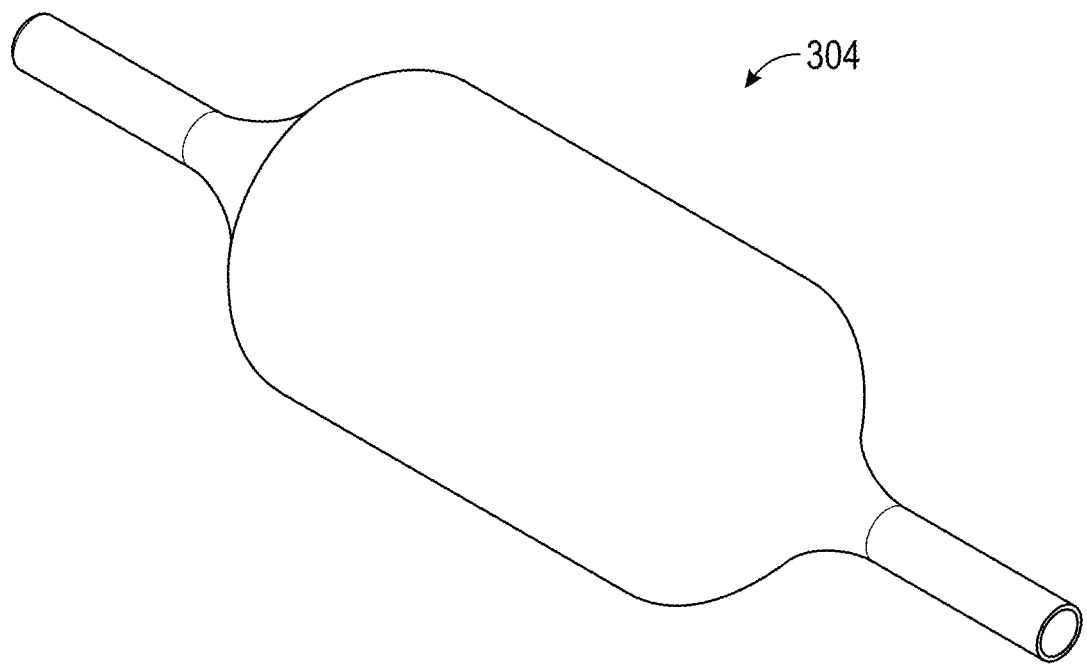
FIG. 24 is a perspective view of a variation of a dilation balloon.
Figure 25:
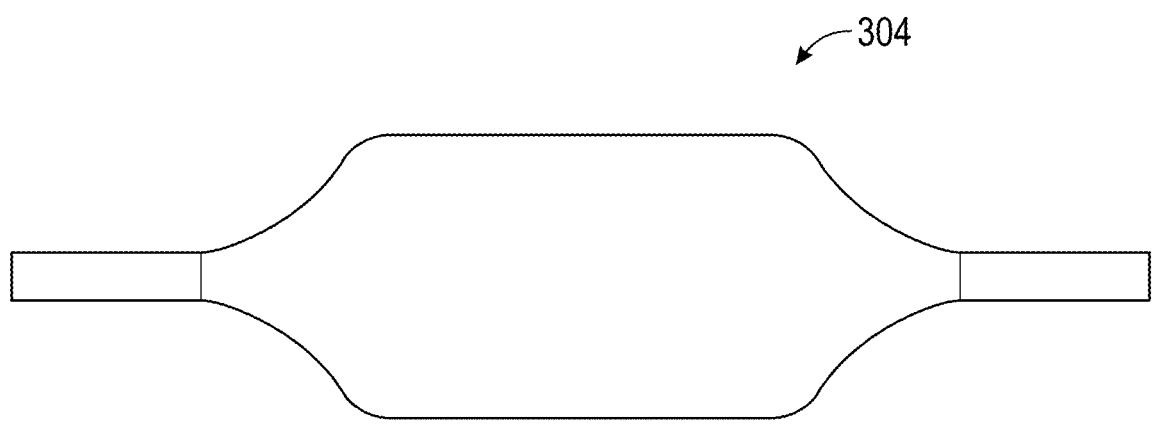
FIG. 25 is a side view of a variation of a dilation balloon.

In some variations, the dilation balloon may have a spherical, spheroid, ellipsoid, or a cylindrical shape with at least one rounded or conical end. In at least one variation, as seen in FIGS. 24 and 25, the dilation balloon 304 may have a conical end, tapering outward to the catheter body at each end. The conical, tapered end may allow the balloon to fold when deflated such that it can fit within a 2.8 mm or 3.2 mm working channel of an endoscope. In another variation, for example as seen in FIG. 21, the dilation balloon 304 may have a generally cylindrical shape with rounded ends. In one variation, as seen in FIGS. 10-12, the proximal end of the dilation balloon 204 may have a generally flat or flat cone shape or be generally be less rounded than the distal end of the dilation balloon 204. In some examples, the proximal end of the dilation balloon may have a lower degree of curvature as compared to a standard dilation balloon. The substantially flat proximal end may allow for an endoscope camera to rest at the proximal end of the balloon and provide a clearer view through dilation balloon for the user. The proximal and the distal ends may be expanded at different rates or pressures and may allow the dilation balloon 204 to have a symmetrical or an asymmetrical shape.

In a variation, at least one of the proximal and distal ends of the dilation balloon may have a generally rounded or bulbous shape. The dilation balloon may include 0, 1, or 2 bulbs at one or both ends of the dilation balloon. The bulbs may have a rounded, conical, frusto-conical, spherical, or frusto-spherical shape. In one variation, the bulbs have a diameter larger than the body of the dilation balloon. In a variation, the proximal and the distal end may each include a bulb, giving the dilation balloon a general barbell type shape when expanded. The bulbs may provide stability and help secure the dilation balloon in the proper location for dilation. The bulbs may further reduce the ability of the balloon to migrate inside the lumen. For example, as seen in FIGS. 13-15, the proximal portion 122 and the distal portion 124 of the dilation balloon may each include a bulb, giving the dilation balloon 104 a general barbell type shape when expanded. In this variation, a pronounced lip 126 may form at the proximal portion 122 and the distal portion 124. The bulbs may provide stability and help secure the dilation balloon 104 in the proper location for dilation. In a variation, the bulbs may aid in properly seating the dilation balloon 104 in papillary opening and the lumen of the hepatopancreatic ampulla when the dilation balloon 104 is in the expanded state. The bulbs on the proximal portion 122 and distal portion 124 of the dilation balloon 104 may further reduce the ability of the balloon to migrate inside the lumen.

The material of the dilation balloon 204 may vary along the length of the balloon to allow for the variation in expansion. The dilation balloon 204 may include polyether block amide (for example, Pebax® 7233), plastics, polyurethane, nylon, any non-latex polymer, or combinations thereof. In one aspect, the expandable dilation balloon 204 may be made of Pebax® 7233. In another aspect, the expandable dilation balloon 204 may be made of a polyurethane and nylon mixture.

In multiple aspects, the dilation balloon may be compliant or non-compliant. The compliance of the dilation balloon 104, 204 may vary with the diameter of the balloon. In various aspects, the compliance of the dilation balloon may range from about 14% to about 60%, from about 15% to about 20%, from about 17% to about 25%, from about 23% to about 33%, and about 30% to about 60%. The larger the diameter of the inflated dilation balloon, the higher the percent compliance, and the smaller the diameter of the inflated dilation balloon, the lower the percent compliance. In an aspect, the combination of plastics in the dilation balloon may be determined based on the desired compliance of the balloon.

In a variation, for example as seen in FIGS. 1-4, 9, and 12, the body/dilating portion of the dilation balloon 104, 204 may include a rough texture on the surface of the balloon induce friction at the stricture site to further secure the dilation balloon when expanded and prevent the balloon from slipping or migrating. In another aspect, the dilating portion of the dilation balloon may expand with a serrated and/or spiral extrusion to induce friction at the stricture site. In one example, the texture or ribbing will create friction and reduce the ability for balloon migration. The dilation balloon 104, 204 may also include protrusions or ribs 210 to increase the surface area of the balloon and therefore have more growth in compliance. The ribs may be concentric rings around the circumference of the dilation balloon, may be a continuous spiral along the length of the dilation balloon, or may be longitudinal protrusions along the length of the dilation balloon. In other aspects, the ribs may be indentions within the balloon. The dilation balloon may have at least 1 rib, at least 2 ribs, at least 3 ribs, at least 4 ribs, at least 5 ribs, at least 6 ribs, or more than 7 ribs. In some aspects, the ribs increase the length and/or the diameter of the dilation balloon when expanded to strengthen the balloon. For example, the ribbing may provide for the dilation balloon to expand an additional 1 mm in diameter as compared to a dilation balloon without ribbing. The ribs may make the dilation balloon stronger or more resistant to popping.

Occlusion Anchor Balloon

The dilation device further includes an occlusion anchor balloon 106, 206, 306. The occlusion anchor balloon may be located proximal to, distal to, or concentric with the dilation balloon at the distal end of the catheter body. In some variations, the occlusion anchor balloon overlaps or surrounds at least a portion of the dilation balloon, as seen in FIGS. 7A, 7B, 8A, 8B, and 9. In at least one variation, the dilation balloon is located inside the occlusion anchor balloon, as seen in FIGS. 22, 23, 27, 30, 31, and 32A-32D. In one variation, the occlusion anchor balloon is distal to the dilation balloon. The occlusion anchor balloon is configured to serve as an anchor for the dilation balloon. In some variations, the occlusion anchor balloon may also be used to determine the size of the dilation of the stricture site by the dilation balloon. In other variations, the occlusion anchor balloon may also serve as an occlusion/extraction balloon 106.

Figure 19:
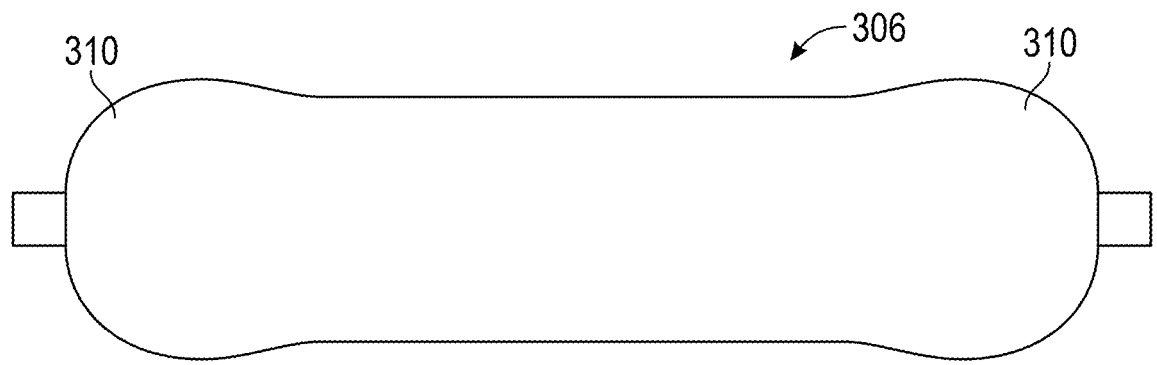
FIG. 19 is a side view of a variation of an occlusion anchor balloon with two bulbs.
Figure 20:
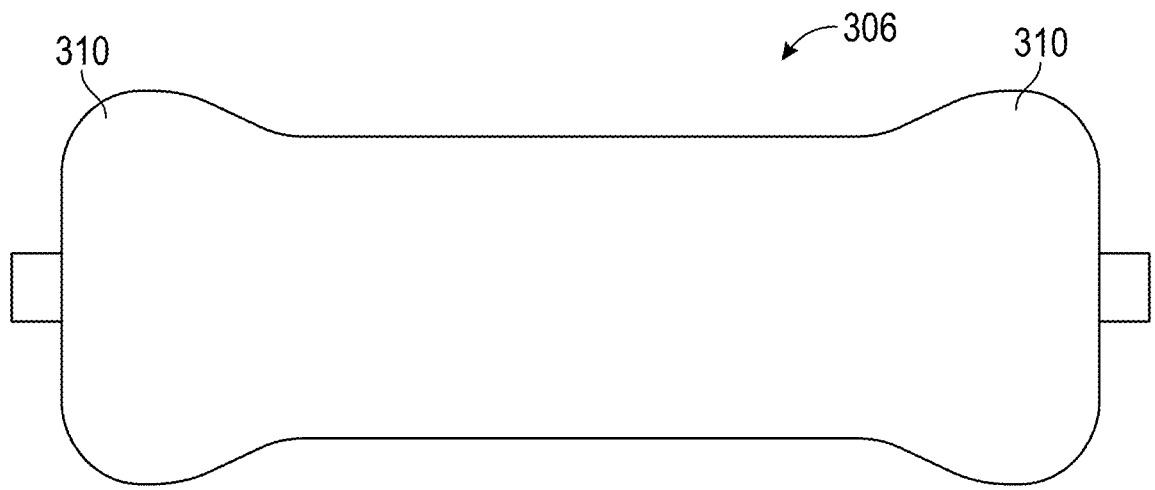
FIG. 20 is a side view of a variation of an occlusion anchor balloon with two bulbs.
Figure 26:
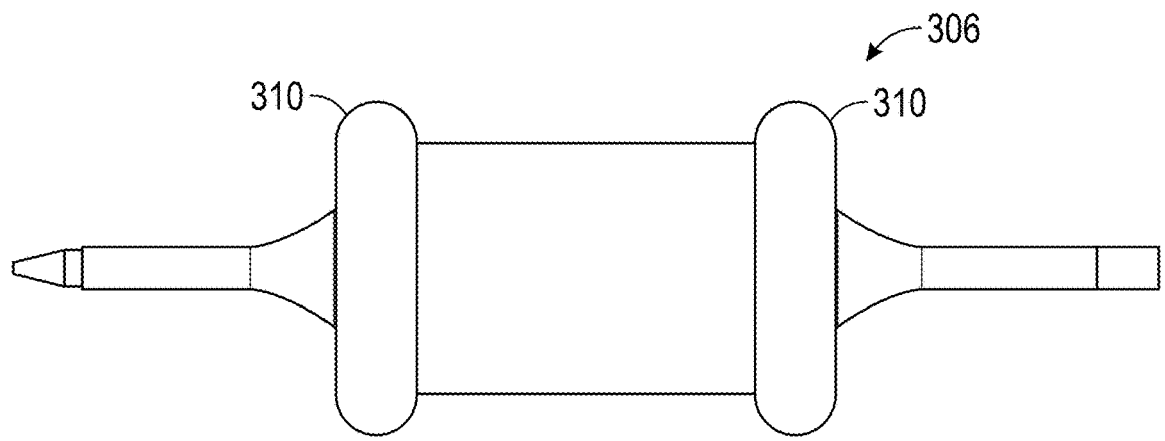
FIG. 26 is a side view of a variation of an occlusion anchor balloon with two bulbs.

In a variation, at least one of the proximal and distal ends of the occlusion anchor balloon may have a generally rounded or bulbous shape. The occlusion anchor balloon may include 0, 1, or 2 bulbs at one or both ends of the body of the occlusion anchor balloon. The body of the occlusion anchor balloon may be generally cylindrical. The bulbs may have a rounded, disk-like, cylindrical, conical, frusto-conical, spherical, or frusto-spherical shape. In one variation, the bulbs have a diameter larger than the body of the occlusion anchor balloon. In another variation, when the occlusion anchor balloon is fully inflated, the bulbs have the same diameter as the body of the occlusion anchor balloon. In a variation, the proximal and the distal end may each include a bulb, giving the occlusion anchor balloon a general barbell type shape when expanded. For example, as seen in FIGS. 19, 20, and 26, the occlusion anchor balloon 306 has a bulb 310 at the proximal and distal end of the occlusion anchor balloon body. In some examples, the bulbs 310 may have a rounded shape like FIG. 19, a frusto-conical shape like FIG. 20, or a shortened cylindrical or disk-like shape in FIG. 26. The bulbs may provide stability and help secure the dilation device in the stricture site for dilation. The bulbs may further minimize or reduce the ability of the dilation balloon to migrate inside the stricture site.

The occlusion anchor balloon is separately expandable from the dilation balloon. The lumen of the occlusion anchor balloon is in fluid communication with at least one lumen of the catheter body 102, 202, 302 through at least one occlusion anchor balloon opening 108, 208, 308 in the catheter body. In some variations, the occlusion anchor balloon may be inflated through more than one occlusion anchor balloon openings, for example, as seen in FIG. 22. The occlusion anchor balloon may be inflated first and separately from the dilation balloon to the diameter prescribed for the dilation of the stricture site.

In an example, the catheter body may be inserted such that both the occlusion anchor balloon and dilation balloon are at the stricture site. In this example, the occlusion anchor balloon surrounds the dilation balloon, such that the two balloons are nested. The occlusion anchor balloon has a bulb at each end of the body of the occlusion anchor balloon and the dilation balloon is within the body of the occlusion anchor balloon, between the two bulbs. The occlusion anchor balloon may then be inflated where the diameter of each of the bulbs is larger than the diameter of the stricture, such that the occlusion anchor balloon keeps the dilation device in place while the dilation balloon is inflated. The use of the occlusion anchor balloon may reduce or prevent dilation balloon migration.

The nesting of the occlusion anchor balloon and the dilation balloon may provide for using a dilation balloon with a length of less than 5 cm and reduce or prevent excess dilation. In some variations, the occlusion anchor balloon may be less than 6 cm. In other variations, the occlusion anchor balloon may be less than 5 cm long. In a variation, the occlusion anchor balloon may be less than 4 cm long. In a variation, the occlusion anchor balloon may be less than 3 cm long. When the dilation balloon is nested in the occlusion anchor balloon, the length of the body of the occlusion anchor balloon (i.e. the length between the two bulbs) may correspond to the net treatment length of the dilation balloon inside the body of the occlusion anchor balloon.

In a variation, the body of the occlusion anchor balloon (i.e. length of the occlusion anchor balloon between the two bulbs) has a length of less than or equal to 2 cm. In a variation, the body of the occlusion anchor balloon has a length of less than or equal to 3 cm. In a variation, the body of the occlusion anchor balloon has a length of less than or equal to 4 cm. In a variation, the body of the occlusion anchor balloon has a length of less than or equal to 5 cm. In a variation, the body of the occlusion anchor balloon has a length of less than or equal to 6 cm. In a variation, the bulbs of the occlusion anchor body may have a length of 2 cm or less. In a variation, the bulbs of the occlusion anchor body may have a length of 1 cm or less. In a variation, the bulbs of the occlusion anchor body may have a length of 0.5 cm or less.

In an example, the catheter body may be inserted such that the body of the occlusion anchor balloon is within the stricture site. The occlusion anchor balloon may then be inflated such that the bulbs are a diameter larger than the diameter of the stricture. The bulbs may be proximal and distal to the stricture site, allowing the net treatment length of the dilation balloon to be fully within the stricture site. In some examples, the bulbs of the occlusion anchor balloon may extend up to 0.5 cm beyond the stricture site in the proximal and/or distal direction. In some examples, the bulbs of the occlusion anchor balloon may extend up to 1 cm beyond the stricture site in the proximal and/or distal direction. In some examples, the bulbs of the occlusion anchor balloon may extend up to 1.5 cm beyond the stricture site in the proximal and/or distal direction. In some examples, the bulbs of the occlusion anchor balloon may extend up to 2 cm beyond the stricture site in the proximal and/or distal direction. In some variations, the occlusion anchor balloon is low pressure and/or compliant such than the anchors outside the stricture site have low to minimal impact on the healthy tissue outside the stricture site. For example, excess dilation is still minimized when the bulbs of the anchor balloon extend in the proximal and distal direction out of the stricture site.

In one example, the catheter body may be inserted such that the occlusion anchor balloon passes through and is distal to the stricture site. The occlusion anchor balloon may then be inflated to a diameter larger than the diameter of the stricture, such that the occlusion anchor balloon remains distal to the stricture site while the dilation balloon is inflated. The catheter body may be pulled to apply a force against the base of the stricture site to secure the occlusion anchor balloon. The use of the occlusion anchor balloon may reduce or prevent dilation balloon migration. The force may be maintained throughout the dilation portion of the procedure. The placement of the occlusion anchor balloon may provide for using a dilation balloon with a length of less than 5 cm and reduce or prevent excess dilation.

In the variation where the occlusion anchor balloon is an occlusion/extraction balloon, the occlusion/extraction balloon 106 is first used to anchor the dilation balloon and then used to retrieve or extract an object. For example, the occlusion/extraction balloon may first anchor the dilation balloon to dilate the papilla, then the dilation balloon is deflated, and the occlusion/extraction balloon is used to extract a stone.

The occlusion anchor balloon may be separated from the dilation balloon by a distance or may be directly welded to the dilation balloon at any point along the length of the dilation balloon. In an aspect, as seen in FIG. 1, FIG. 4, FIGS. 13-15, and FIG. 18, the dilation balloon 104, 204 and the occlusion anchor balloon 106, 206 may be each welded to the catheter body 102, 202 but separated from each other by a distance. The distance between the two balloons may vary from about 0.5 mm to about 1 mm, from about 1 mm to about 3 mm, from about 2 mm to about 4 mm, from about 3 mm to about 5 mm, and from about 5 mm to about 10 mm, from about 10 mm to about 20 mm, or from about 20 mm to about 30 mm. In one variation, the distance between the two balloons is 0.5 mm to 1 mm. In other variations where the occlusion anchor balloon also is used for extraction, the distance between the two balloons may be 0.5 cm to 1 cm.

The dilation balloon and the occlusion anchor balloon may each be separately attached to the catheter body and to each other. In some variations, as seen in FIG. 2, FIG. 3, FIGS. 7-9, FIGS. 22-23, 27, and FIGS. 30-32, the dilation balloon 204, 304 and the occlusion anchor balloon 206, 306 may be each welded to the catheter body 202, 302 and laser welded to each other. The proximal end of the occlusion anchor balloon may be externally connected to the distal end, proximal end, or any point between the distal end and proximal end of the dilation balloon. The balloons may be connected such that there is an overlap between balloons for at least a portion of the length of the dilation balloon. For example, in FIGS. 2, 3, and 9, the proximal end of the occlusion anchor balloon is attached to the distal end of the dilation balloon while in FIGS. 7A, 7B, 8A, and 8B, the proximal end of the occlusion anchor balloon is attached to the proximal end of the dilation balloon. When the proximal end of the occlusion anchor balloon is connected to the external surface of the proximal end of the dilation balloon or when the balloons are nested, there is a thickness of two balloons around the dilation balloon for at least a portion of the length of the dilation balloon. In some variations, the occlusion anchor balloon may completely surround the dilation balloon, such that there is full overlap of the balloons. For example, the dilation balloon 304 may be nested within the body of the occlusion anchor balloon 306, as seen in FIGS. 22-23, 27, and 30-32. When the balloons are nested, there is a thickness of two balloons around the dilation balloon for the entire length of the dilation balloon. Without being limited to a particular theory, the double balloon thickness may provide additional strength for the dilation balloon. The nesting of the dilation balloon and occlusion anchor balloon allows the anchor balloon to anchor the dilation balloon directly in the stricture site. Consequently, the dilation balloon can be reduced in length to match the length of the stricture site to reduce or minimize excess dilation of healthy tissue beyond the stricture site. In some variations, the dilation expandable body, when expanded, extends no more than 1 cm beyond the stricture site in either the proximal or distal direction.

There may be an about 0.5 mm to about 6 cm overlap between the two balloons. In various aspects, the overlap between the occlusion anchor balloon and the dilation balloon may be at least about 0.5 mm, at least about 1 mm, at least about 5 mm, at least about 1 cm, at least about 3 cm, or at least about 5 cm. In other aspects, the overlap may be less than or equal to 1 mm, less than or equal to 5 mm, less than or equal to 1 cm, less than or equal to 3 cm, or less than or equal to 6 mm. Although the two balloons may be connected externally, they are individually and separately inflated.

The occlusion anchor balloon may have a shape and size that varies from the dilation balloon. In various aspects, the occlusion anchor balloon 106, 206 may have a spherical, spheroid, ellipsoid, conical, cylindrical, oblong, barbell, or asymmetrical shape. In one variation, the occlusion anchor balloon may be tapered from the distal end to the proximal end as seen in FIGS. 7A-8B. In another variation, the occlusion anchor balloon may have a bulb on both the proximal and distal end as seen in FIGS. 19-20 and 26. The shape of the occlusion anchor balloon may be determined by the location of where it is welded to the dilation balloon. The occlusion anchor balloon may have a shape and size that varies from the dilation balloon.

The occlusion anchor balloon may be expanded until it reaches the diameter of the desired dilation of the stricture site. The occlusion anchor balloon is configured to be filled with saline, air, or a contrast/saline mixture. The dilation device may further include a bleed valve to release any extra air pushed through the syringe beyond the set volume needed to expand the occlusion anchor balloon to the proper diameter. The occlusion anchor balloon has the ability to be expanded to a wide range of diameters and be able to easily change between diameters. In one example, the occlusion/extraction balloon 106 may expand to the diameter of the biliary duct at a target site, such that contrast dye injected from a guide wire or dye opening distal to the occlusion/extraction balloon 106 remains distal to the balloon and contrast dye injected from a dye opening proximal to the extraction balloon 106 remains proximal to the balloon.

The occlusion anchor balloon may be expanded to diameters ranging from about 0.5 mm to about 25 mm. In various aspects, the occlusion anchor balloon may be inflated to a diameter of at least about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, and about 25 mm. In one variation, the occlusion anchor balloon may have an inflation diameter range of 15-20 mm±2 mm. In some variations, the occlusion anchor balloon may have a set inflation diameter of 18 mm, 19 mm, 20 mm, 21 mm, 22 mm, 23 mm, 24 mm, and/or 25 mm.

In an aspect, the occlusion anchor balloon may have a length of at least about 0.5 cm, at least about 1 cm, at least about 2 cm, at least about 3 cm, at least about 4 cm, at least about 5 cm, or at least about 6 cm. In one aspect, the occlusion anchor balloon has a length of about 1 cm. When at least a portion of the occlusion anchor balloon extends over the dilation balloon, the occlusion anchor balloon may have a length of at least about 2 cm. In a variation, when the occlusion anchor balloon surrounds the dilation balloon, the occlusion anchor balloon has a length of up to 3 cm or 4 cm or any length capable of completely surrounding the dilation balloon.

The occlusion anchor balloon may be made of polyurethane. This material allows for the balloon to be welded to the catheter body and withstand internal pressures when in the expanded state. In a variation, the occlusion anchor balloon may be thermos-welded around the circumference of the catheter body at at least two locations. In another variation, the occlusion anchor balloon may be thermo welded to the catheter body at one location and laser welded to the dilation balloon at another location. The occlusion anchor balloon may be inflated with air or a fluid, such as saline. This may allow for the balloon to be expanded to specific diameters. For example, the amount of saline or air injected though a lumen of the catheter body into the occlusion anchor balloon may correspond to an inflation diameter of the occlusion anchor balloon. This may provide the doctor with the ability to know the diameter of the occlusion anchor balloon by the volume of saline injected. The polyurethane material and saline fill may provide for improved resistance to puncture or deflation during use. The occlusion anchor balloon may be nonreactive with the saline. In some variations, the occlusion anchor balloon may be further treated or have added features to increase the strength of the balloon, in particular when it is used as an occlusion/extraction balloon to reduce the likelihood of popping upon retrieval of an object. After dilation, the occlusion anchor balloon may be reduced in size by drawing the saline back through the catheter body and into the syringe used for delivery of the saline.

In an aspect, at least one of the expandable bodies may include at least one radiopaque marker 128, 228, including but not limited to a radiopaque medical ink or barium sulfate. In an aspect, an expandable body may include more than one radiopaque marker 228 spaced a distance from one another. When the expandable body is inflated, the distance between the radiopaque markers may increase, allowing the surgeon to determine the amount the expandable body has been inflated. The radiopaque marking may include a single marker that increases in surface area as the expandable body increases in volume. In another aspect, the radiopaque marker 228 may be used to locate at least one of the expandable bodies within the patient. In one aspect, the dilation balloon 204 and the occlusion anchor balloon 206 each have a radiopaque marker band 228. The radiopaque marker 228 may be located in the center of the dilation balloon 204 and/or the occlusion anchor balloon 206. In other aspects, the ribs or texture of the dilation balloon 204 may include radiopaque dye.

Manifold

The dilation device may include a manifold 132, 232, 323 for injection of the compressible or incompressible fluids to the dilation balloon and the occlusion anchor balloon. The manifold may also provide for the injection of the contrast dye to the target site and/or use of a guide wire.

The manifold may include at least two ports connected to at least two lumina of the catheter body for expanding the dilation balloon and the occlusion anchor balloon. In an aspect, the dilation device may include two ports connected to the catheter body corresponding to the dilation balloon and the occlusion anchor balloon. In one variation, the dilation balloon and the occlusion anchor balloon are filled using the same port. In another variation, the dilation device may include three ports connected to the catheter body corresponding to the dilation balloon, the occlusion anchor balloon, and a guide wire and/or dye opening.

As seen in FIGS. 5, 9, and 7A-8B, the at least two ports 234, 236 may be located on a manifold 232 connected to the proximal portion of the catheter body 202 and in fluid communication with the lumina of the catheter body 202. For example, FIGS. 5A and 5B show one manifold variation. This manifold may include a toggle switch to change the connection of the port to different lumen within the catheter. Therefore, both the occlusion anchor balloon and the dilation balloon may both be expanded using a single port on the manifold.

Figure 28:
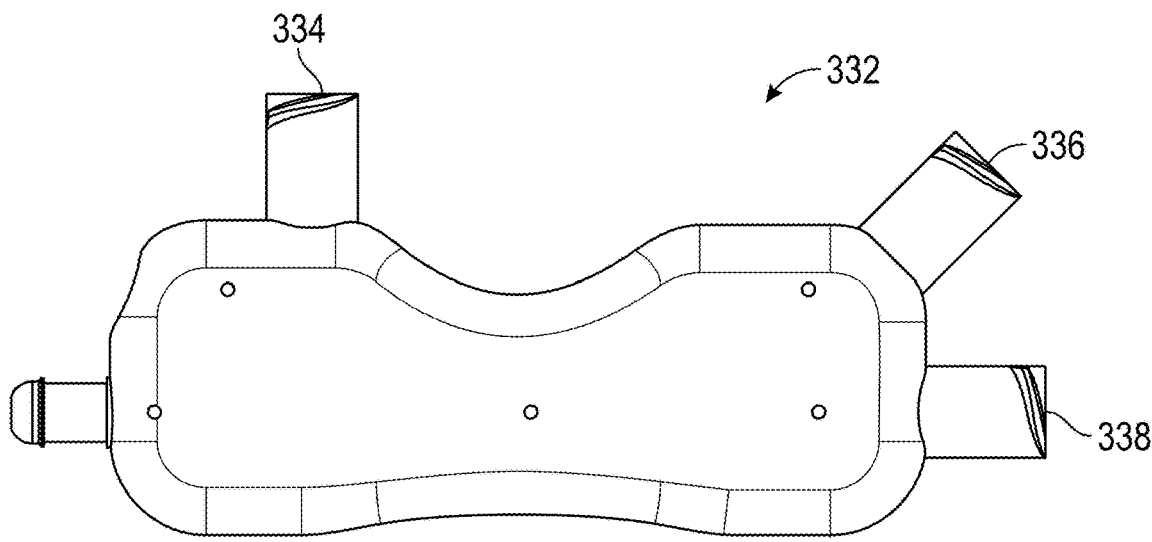
FIG. 28 is side view of a variation of the manifold of the dilation device.
Figure 29:
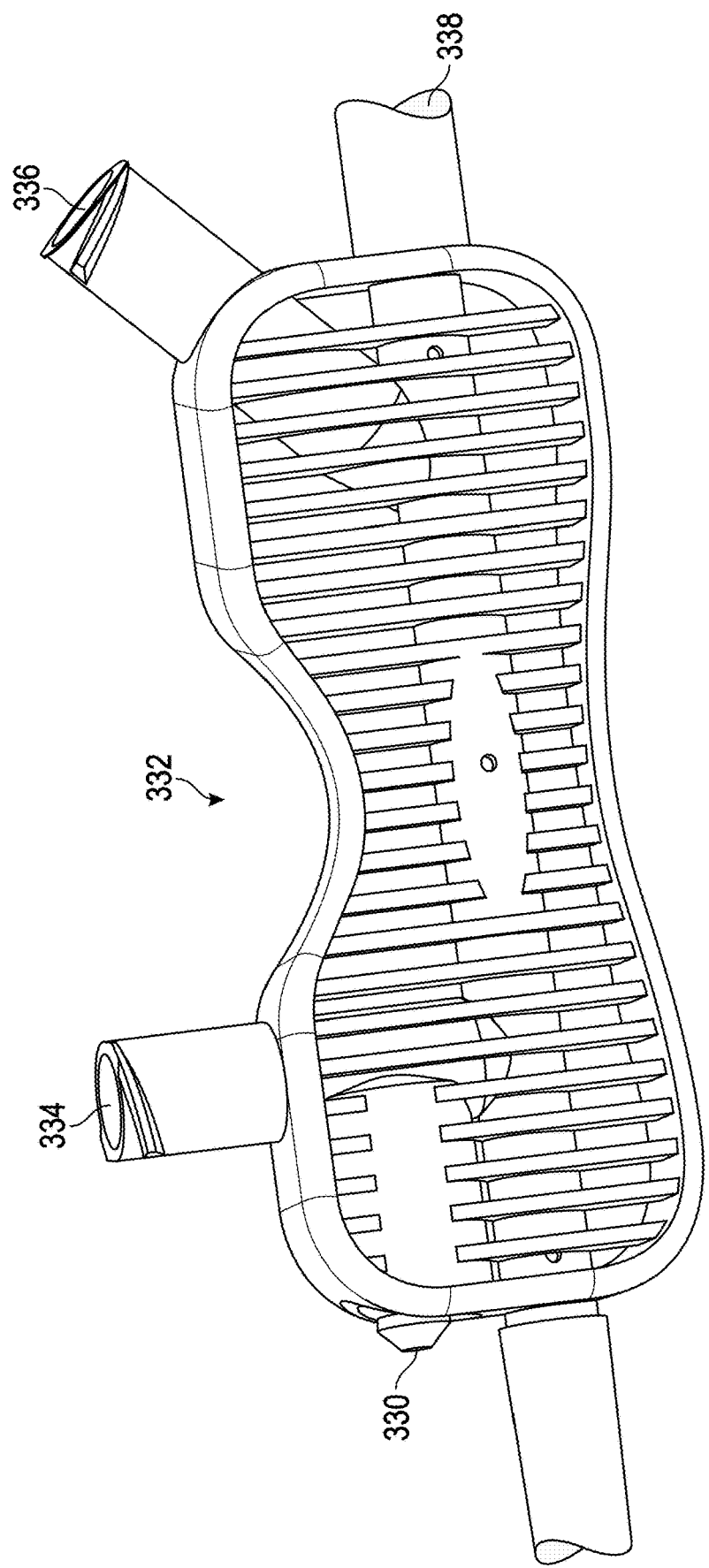
FIG. 29 is a cross-sectional view of a variation of the manifold of the dilation device.

As seen in FIGS. 28-31, the at least two ports 334, 336 may be located on a manifold or handle 332 connected to the proximal portion of the catheter body 302 and in fluid communication with the lumina of the catheter body 302. For example, FIGS. 28 and 29 show one manifold variation. The occlusion anchor balloon port 334 may be fluidly connected to the occlusion anchor balloon through the catheter body and corresponding occlusion anchor balloon opening(s). The occlusion anchor balloon port 334 may be operable to connect to a standard syringe. In an example, the occlusion anchor balloon port 334 may connect to an 8 cc or 10 cc syringe. This manifold 332 may further include a bleed valve 330 connected to the port 334 for filling the occlusion anchor balloon 306. The bleed valve 330 may allow for the occlusion anchor balloon to be inflated by a user without risk of over inflation. For example, once the proper volume of air has been administered through a syringe on the port 334, the remainder of any air pushed through the syringe will exit through the bleed valve 330.

As seen in FIGS. 28 and 29, the port 336 for filling the dilation balloon 304 may be located at a distance from the port for the occlusion anchor balloon 306. In some examples, the manifold 332 may need to be rotated for a user to be able to access the dilation balloon port 336 after filling the occlusion anchor balloon. The dilation balloon port 338 may be operable to connect to a standard balloon inflator. The inflator may be operable to display the pressure value for the fluid or air being delivered to the dilation balloon.

As seen in FIGS. 28 and 29, the manifold 332 may also include a port 338 for a guide wire and or dye.

The manifold may be made of a carbonate or polycarbonate material. In an aspect, a syringe or pressure gun/inflator may detachably connect to each port on the manifold. The ports may have a male or female Leur lock connection for easy attachment of a syringe. Each port on the manifold may be in fluid communication with one lumen of the catheter body. In other variations, a port on the manifold may be capable of being in fluid communication with more than one lumen of the catheter body.

In one aspect, a syringe filled with saline or air may be connected to the port on the manifold in fluid communication with the lumen associated with the occlusion anchor balloon opening, such that when saline or air is ejected from the syringe, the occlusion anchor balloon is inflated. In an aspect, a syringe or pressure gun/inflator may be connected to the port on the manifold in fluid communication with the lumen associated with the dilation balloon opening, such that when a fluid or air is delivered from the gun, the dilation balloon is inflated. In one variation, the syringe or pressure gun used to inflate the dilation balloon may be connected to the same port that was used to inflate the occlusion anchor balloon after the syringe to inflate the occlusion anchor balloon is removed from the port and the toggle switch is adjusted to change the lumen that the port is fluidly connected to. In another variation, the occlusion anchor balloon and dilation balloon are inflated using separate ports. Once the occlusion anchor balloon is inflated with a syringe attached to the occlusion anchor balloon port, the manifold is rotated and an inflator is connected to the dilation balloon port for inflation of the dilation balloon. A pressure gun/inflator may be used over a syringe for inflating the dilation balloon because the pressures needed to achieve the desired dilation may be difficult to be achieved by hand. In another variation, a syringe filled with contrast dye may be connected to the port on the manifold in fluid communication with the lumen associated with the guide wire or contrast dye opening, such that when the contrast dye is ejected from the syringe, the contrast dye is dispersed around the target site.

Methods of Using the Dilation Device

The dilation device may be used to dilate a stricture site, such as the esophagus, colon, a papillary opening, and/or a biliary duct. An endoscope may be utilized to navigate the dilation device to a target area that includes the stricture site. The dilation device may then be deployed through the endoscope and into the stricture site for dilation of the stricture site.

The expandable bodies may be first introduced in a non-expanded state into a patient using the dilation device and endoscope. A guide wire may be extended through the endoscope to the desired site to aid in navigating the catheter body of the device. The catheter body may be negotiated with the expandable bodies in the non-expanded state to the target area. A contrast dye may be injected through the catheter body and out a dye opening to allow imaging of portions of the target area or may be mixed with a fluid used to inflate one of the expandable bodies.

In one variation, as illustrated in FIGS. 6A-6C, the dilation device is deployed until the occlusion anchor balloon is beyond the stricture site. The occlusion anchor balloon is then expanded to a diameter. The diameter of expansion may be determined by prior or concurrent visualization of the stricture site. For example, the occlusion anchor balloon is expanded to a diameter larger than the diameter of the stricture site and the diameter of the desired dilation. The dilation device may then be pulled by the user such that the expanded occlusion anchor balloon is seated against the distal end of the stricture site and/or a lumen just beyond the stricture distal funnel. In one variation, the shape of the occlusion anchor balloon may assist in anchoring the dilation device. Once the occlusion anchor balloon is seated properly, this will also allow the dilation balloon to also be seated properly within the stricture site. The user may keep hold of the catheter, pulling the occlusion anchor balloon against the stricture site during the dilation process.

Figure 32A:
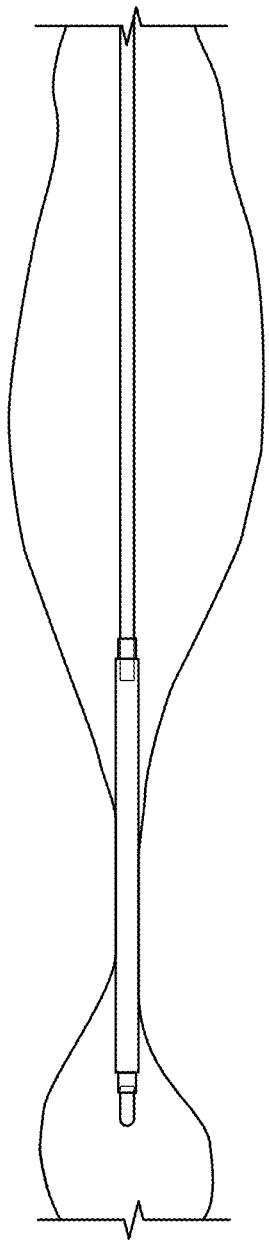
FIG. 32A shows the dilation device with the dilation balloon and the occlusion anchor balloon deflated at a stricture site in one variation.
Figure 32B:
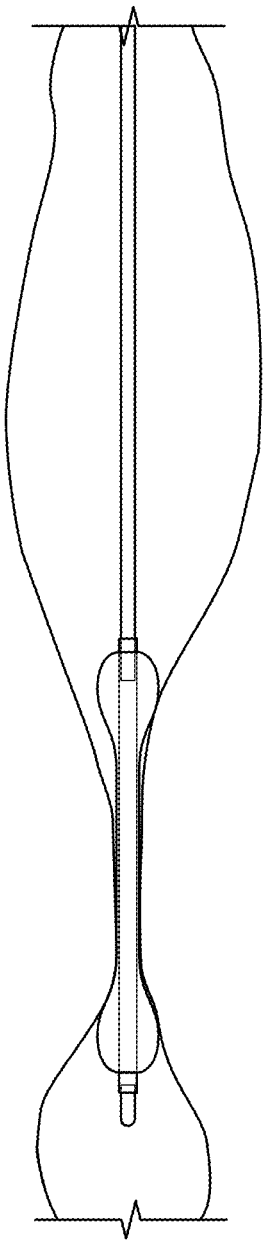
FIG. 32B shows the dilation device with the occlusion anchor balloon partially inflated and the dilation balloon deflated in one variation.
Figure 32C:
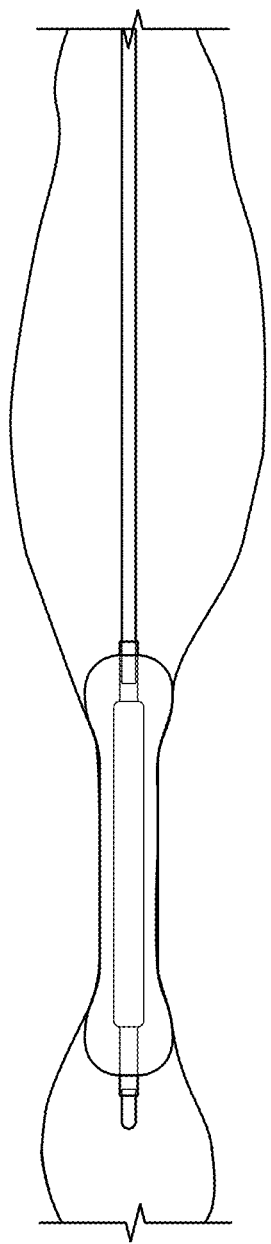
FIG. 32C shows the dilation device with the occlusion anchor balloon fully inflated and the inner balloon partially inflated in one variation.
Figure 32D:
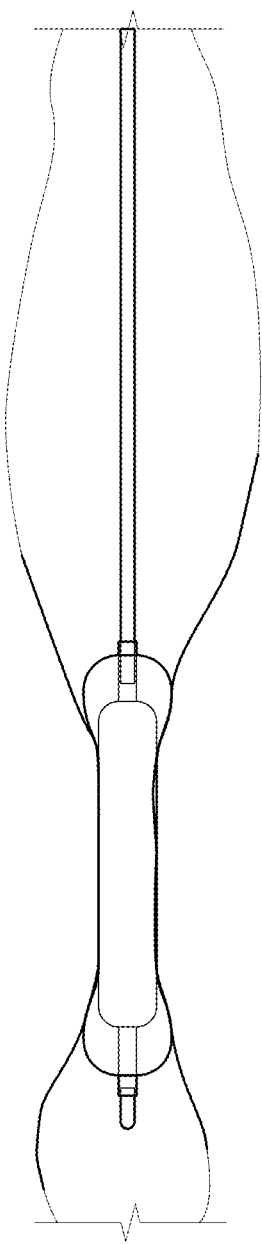
FIG. 32D shows the dilation device with the dilation balloon and occlusion anchor balloon fully inflated in one variation.

In another variation, as illustrated in FIG. 32A, when the occlusion anchor balloon surrounds the dilation balloon, the dilation device is deployed until both the occlusion anchor balloon and dilation balloon are at the stricture site in the deflated state. As seen in FIGS. 32B and 32C, the occlusion anchor balloon may then be inflated, such that the occlusion anchor balloon keeps the dilation device in place within the stricture. The inflation of the occlusion anchor balloon may slightly expand the dilation balloon due to changing pressures in the dilation device. Once the occlusion anchor balloon secures the dilation device, the dilation balloon is inflated, as seen in FIG. 32D.

The use of the occlusion anchor balloon allows reduces or prevents migration of the dilation balloon while dilating and may reduce or prevent excess dilation. The dilation balloon is inflated and then deflated until the stricture is treated. A camera from the scope may be positioned at the proximal end of the dilation balloon to observe the dilation device and stricture site during dilation. After dilation, in one variation, the occlusion anchor balloon may then be used to pull through the stricture for sizing the dilation.

In one variation, the dilation and extraction device may be used to dilate a papillary opening and/or a biliary duct and retrieve an object from the biliary system. In the case of the papillary dilation, the occlusion anchor balloon may be proximal to the dilation balloon. During this procedure, the catheter may be inserted so that the occlusion anchor balloon is placed proximal to the papilla. The dilation balloon 104 may be inserted into the papillary opening in the non-expanded state and then expanded for dilation of the papillary opening. The dilation balloon 104 may be inserted such that at least a portion of the length of the dilation balloon 104 is within the hepatopancreatic ampulla during papillary dilation.

The expandable bodies may be expanded at the stricture site into an expanded state by a fluid or air injected through the catheter body. For example, the dilation balloon may be expanded by the injection of air and/or a fluid through the catheter body from a pressure gun/inflator detachably connected to the manifold and the occlusion anchor balloon may be expanded by the injection of air and/or a fluid through the catheter body from a syringe detachably connected to the manifold.

After dilation, the expandable bodies may return to the non-expanded state, and the dilation device and endoscope may be removed from the body. In one example, both the occlusion anchor balloon and dilation balloon are deflated and the dilation device is removed from the patient's body. In a variation, at least one expandable body may optionally be deflated to the non-expanded state before further movement of the device. In an example, the dilation balloon may be deflated after dilation is achieved and the occlusion anchor balloon will remain inflated to the prescribed dilation diameter of the stricture. The catheter may then be retracted by pulling the occlusion anchor balloon through the stricture site to accurately size the stricture post dilation. Should the sizing prove to be insufficient, the method may be repeated until the operator is satisfied with the dilation sizing. At that time the anchor balloon may be deflated and the catheter may be removed from the patient.

When the occlusion anchor balloon is an occlusion/extraction balloon, the occlusion/extraction balloon may remain expanded while withdrawing the dilation device from the biliary system, such that an object is urged or pulled along with the occlusion/expandable body and removed from the biliary system. For example, the occlusion/extraction balloon, once expanded, may remain in the expanded state in order to retrieve the object from the biliary system. However, the occlusion/extraction balloon may change diameter during the retrieval process to accommodate the varying size of the biliary system. The object may exit the biliary system through the papillary opening and enter the duodenum for removal though the natural solid waste removal process. After removal of the object into the duodenum, the occlusion/extraction balloon may return to the non-expanded state, and the dilation device and endoscope may be removed from the body. In one example, should the operator encounter more distal strictures, the dilation device may be deployed proximal to the stricture into the common bile duct for treatment of additional biliary strictures.

EXAMPLES

Example 1: Pressure Analysis

Several parameters were measured for a dilation balloon having a diameter ranging from 15 mm to 25 mm. Table 3 provides the results of the measurements.

TABLE 3

| Balloon Diameter (mm) | Balloon Length (mm) | Surface Area (mm) | Surface Area (Square Inch) | Pressure (Athmosphere) | Pressure (Pound-Force per Square Inch | Total force acting on Balloon (Pound-Force) | N |
|---|---|---|---|---|---|---|---|
| 15 | 40 | 1884.956 | 2.921681118 | 0.5 | 7.34795 | 21.46836677 | 95.3624852 |
| 16 | 40 | 2010.619 | 3.116459859 | 1 | 14.6959 | 45.79918244 | 203.4399684 |
| 17 | 40 | 2136.283 | 3.3112386 | 1.5 | 22.04385 | 72.99244702 | 324.2324497 |
| 18 | 40 | 2261.947 | 3.506017342 | 2 | 29.3918 | 103.0481605 | 457.7399289 |
| 19 | 40 | 2387.61 | 3.700796083 | 2.5 | 36.73975 | 135.9663229 | 603.9624062 |
| 20 | 40 | 2513.274 | 3.895574824 | 3 | 44.0877 | 171.7469342 | 762.8998816 |
| 25 | 40 | 3141.593 | 4.86946853 | 4 | 58.7836 | 286.2448903 | 1271.499803 |

Having described several variations, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed variations teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A dilation device, comprising:
    a gastrointestinal endoscope comprising a working channel;
    a catheter body configured to fit in the working channel of the endoscope, the catheter body comprising a proximal portion and a distal portion, the catheter body having at least two lumina;
    two expandable bodies consisting of:

a dilation expandable body in fluid communication with a first opening on the distal portion of the catheter body; and an occlusion anchor expandable body in fluid communication with a second opening on the distal portion of the catheter body such that the dilation expandable body and occlusion anchor expandable body are separately expandable, wherein the dilation expandable body and occlusion anchor expandable body are configured to be in a nonexpanded state within the working channel of the endoscope, wherein the occlusion anchor expandable body comprises a distal bulb a proximal bulb, and a body portion extending between the distal bulb and the proximal bulb, the distal bulb configured to expand distal to a stricture site and the proximal bulb configured to expand proximal to the stricture site, wherein, when the distal bulb and the proximal bulb are fully inflated, the distal bulb diameter and the proximal bulb diameter are each greater than a diameter of the body portion of the occlusion anchor expandable body, and a fully-inflated distal bulb and a fully-inflated proximal bulb are configured to anchor the occlusion anchor expandable body in the stricture site, wherein the dilation expandable body is operable to expand within the body portion of the occlusion anchor expandable body to dilate the stricture site between the distal bulb and the proximal bulb of the occlusion anchor expandable body, and wherein the occlusion anchor expandable body surrounds the dilation expandable body such that the dilation expandable body is inside the occlusion anchor expandable body.

2. The dilation device of claim 1, further comprising a manifold with at least two ports connected to the proximal portion of the catheter body, each in fluid communication with at least one of the lumina of the catheter body.

3. The dilation device of claim 1, wherein the dilation expandable body expands to a diameter of at least 3 mm to at least 5 mm.

4. The dilation device of claim 1, wherein the dilation expandable body expands to a diameter of 0.5 mm to 25 mm.

5. The dilation device of claim 1, wherein the occlusion anchor expandable body expands to a diameter of 0.5 mm to 25 mm.

6. The dilation device of claim 1, wherein the dilation expandable body is between 0.5 cm and 5 cm in length.

7. The dilation device of claim 1, wherein the length of each bulb is 1 cm or less.

8. The dilation device of claim 1, wherein the dilation expandable body has a net treatment length of 1 cm to 4 cm.

9. The dilation device of claim 1, wherein the occlusion anchor expandable body is operable to reduce migration of the dilation expandable body at the distal end of the stricture site when expanded in the stricture site.

10. The dilation device of claim 1, wherein the dilation device is operable to eliminate migration of the dilation expandable body when expanded.

11. The dilation device of claim 1, wherein the dilation expandable body, when expanded, extends no more than 1 cm beyond the stricture site in either the proximal or distal direction.

12. A method of dilating a stricture site in a patient, comprising:
   inserting the dilation device of claim 1 into a patient;
   expanding the occlusion anchor expandable body; and
   expanding the dilation expandable body at the stricture site.

13. The method of claim 12, further comprising inserting the dilation device through a working channel of an endoscope.

14. The method of claim 12, wherein the dilation expandable body is expanded using fluid or air delivered from a lumen of the catheter body and the occlusion anchor expandable body is expanded using a fluid or air delivered from a separate lumen of the catheter body.

15. The method of claim 12, wherein the dilation expandable body expands to a diameter of 0.5 mm to 25 mm and the occlusion anchor expandable body expands to a diameter of 0.5 mm to 25 mm.

16. The method of claim 12, further comprising deflating the dilation expandable body and the occlusion anchor expandable body.

17. The dilation device of claim 1, wherein the occlusion anchor expandable body includes at least one radiopaque marker.

18. The dilation device of claim 17, wherein the at least one radiopaque marker includes a plurality of radiopaque markers spaced apart from one another such that when the occlusion anchor expandable body is expanded, a distance between individual ones of the plurality of radiopaque markers increases.

19. The dilation device of claim 1, wherein a distal pronounced lip is formed at the distal portion of the catheter body when the distal bulb is expanded distal to the stricture site.

20. The dilation device of claim 1, wherein a proximal pronounced lip is formed at the proximal portion of the catheter body when the proximal bulb is expanded proximal to the stricture site.

21. The dilation device of claim 1, wherein the length of each bulb is 2 cm or less.

* * * * *